United States Patent
Al-Babili et al.

(10) Patent No.: US 11,324,216 B2
(45) Date of Patent: May 10, 2022

(54) METHODS FOR CONTROLLING ROOT PARASITIC WEEDS: INHIBITORS OF SEED GERMINATION IN STRIGA

(71) Applicant: King Abdullah University of Science and Technology, Thuwal (SA)

(72) Inventors: Salim Al-Babili, Thuwal (SA); Stefan Theodor Arold, Thuwal (SA); Umar Farook Shahul Hameed, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 184 days.

(21) Appl. No.: 16/604,706

(22) PCT Filed: Apr. 6, 2018

(86) PCT No.: PCT/IB2018/052425
§ 371 (c)(1),
(2) Date: Oct. 11, 2019

(87) PCT Pub. No.: WO2018/189638
PCT Pub. Date: Oct. 18, 2018

(65) Prior Publication Data
US 2021/0112807 A1    Apr. 22, 2021

Related U.S. Application Data

(60) Provisional application No. 62/484,173, filed on Apr. 11, 2017, provisional application No. 62/641,491, filed on Mar. 12, 2018.

(51) Int. Cl.
*A01N 37/38* (2006.01)
*A01N 31/14* (2006.01)
*A01N 35/02* (2006.01)
*C07C 43/23* (2006.01)
*C07C 49/255* (2006.01)
*C07C 59/68* (2006.01)
*A01G 7/06* (2006.01)

(52) U.S. Cl.
CPC ............ *A01N 37/38* (2013.01); *A01G 7/06* (2013.01); *A01N 31/14* (2013.01); *A01N 35/02* (2013.01); *C07C 43/23* (2013.01); *C07C 49/255* (2013.01); *C07C 59/68* (2013.01)

(58) Field of Classification Search
None
See application file for complete search history.

(56) References Cited

U.S. PATENT DOCUMENTS 3,075,878 A    1/1963   Ziffer
2010/0009853 A1  1/2010   Ikeda et al.

FOREIGN PATENT DOCUMENTS

EP    2351484    8/2011

OTHER PUBLICATIONS

International Search Report for corresponding PCT application PCT/IB2018/052425 dated Aug. 20, 2018.
Buchanan, "Patterns of Surfactant Toxicity to Plant Tissues", Thesis, 1-210 (1965).
Feruzan, et al., "Phytotoxic Effects of Non-ionic Surfactant Octylphenol Series (Triton X-100, Triton X-114, Triton X-405) on Onion", Asian Journal of Chemistry, 24(12):5746-5748 (2012).

*Primary Examiner* — Alton N Pryor
(74) *Attorney, Agent, or Firm* — Pabst Patent Group LLP

(57) ABSTRACT

Herbicides, systems, and methods for inhibiting germination of a root parasitic plant are provided. In particular, the herbicide includes an active compound represented by Formula I. In this regard, the active compound is selected to bind to an active site of strigolactone receptors in seeds of the root parasitic plant.

10 Claims, 12 Drawing Sheets

Figure 1:
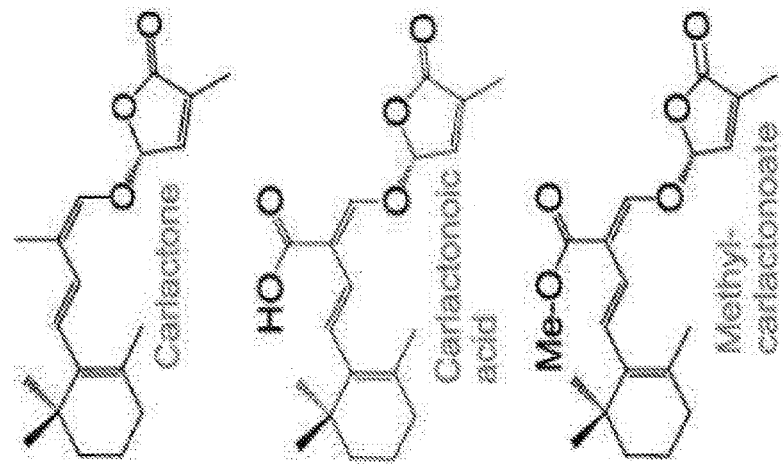
Figure 1:
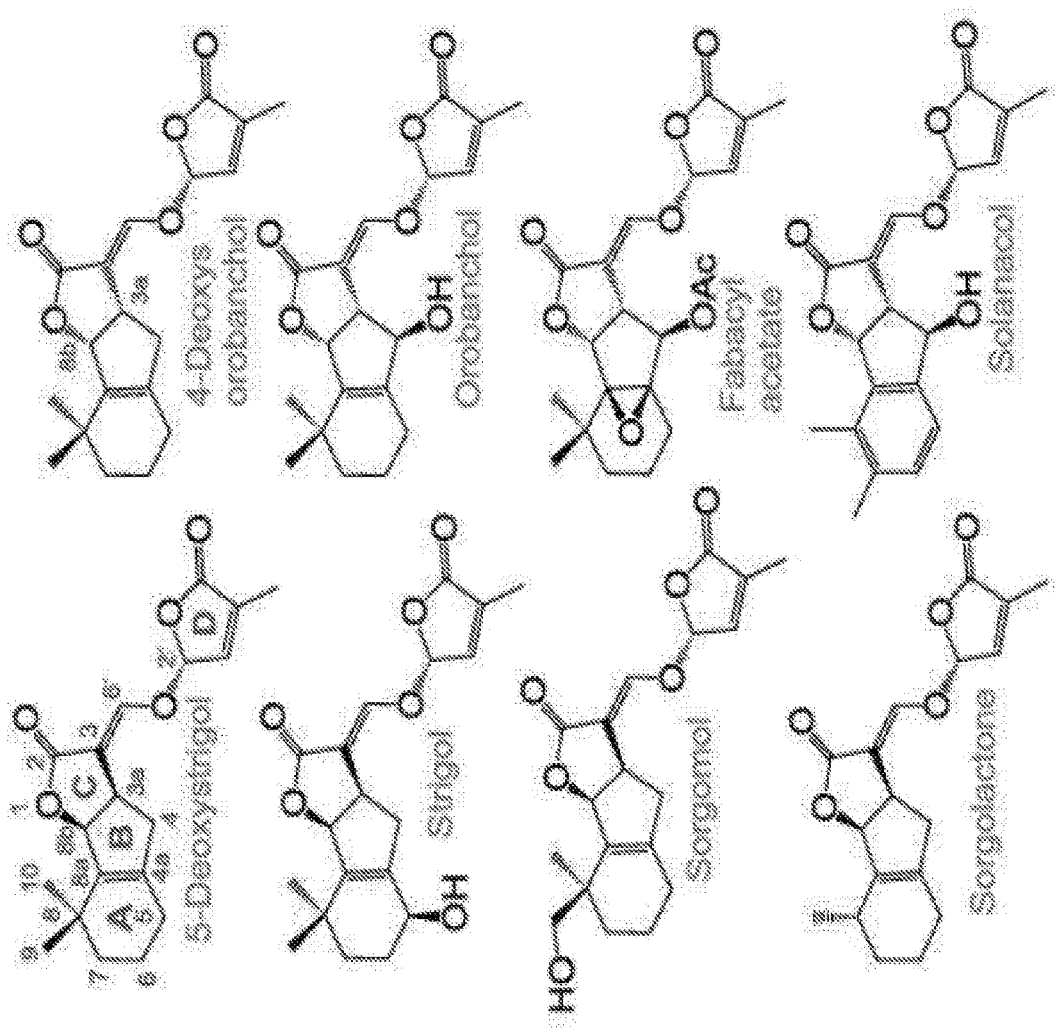
Figure 2:
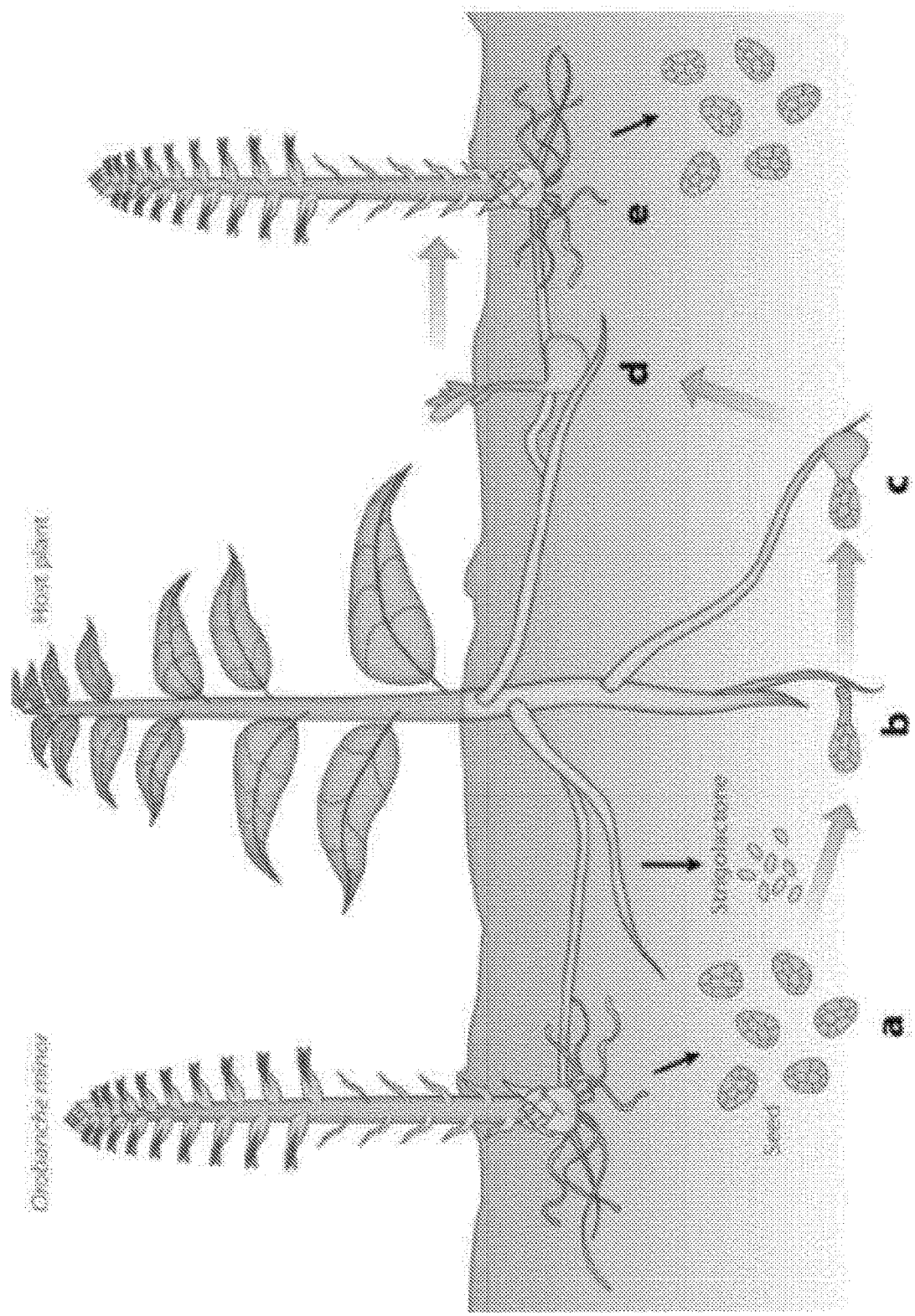
Figure 3:
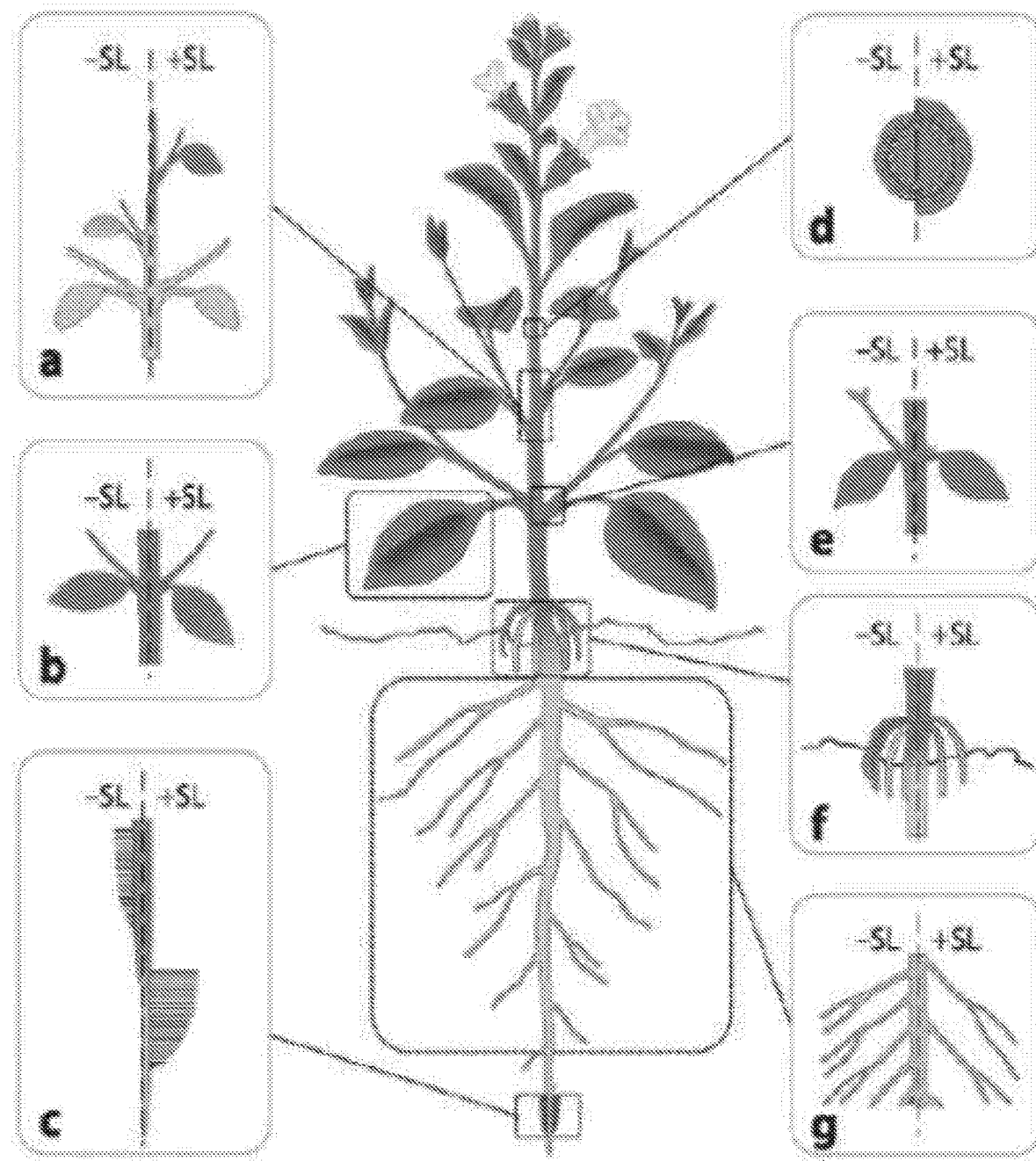
Figure 4:
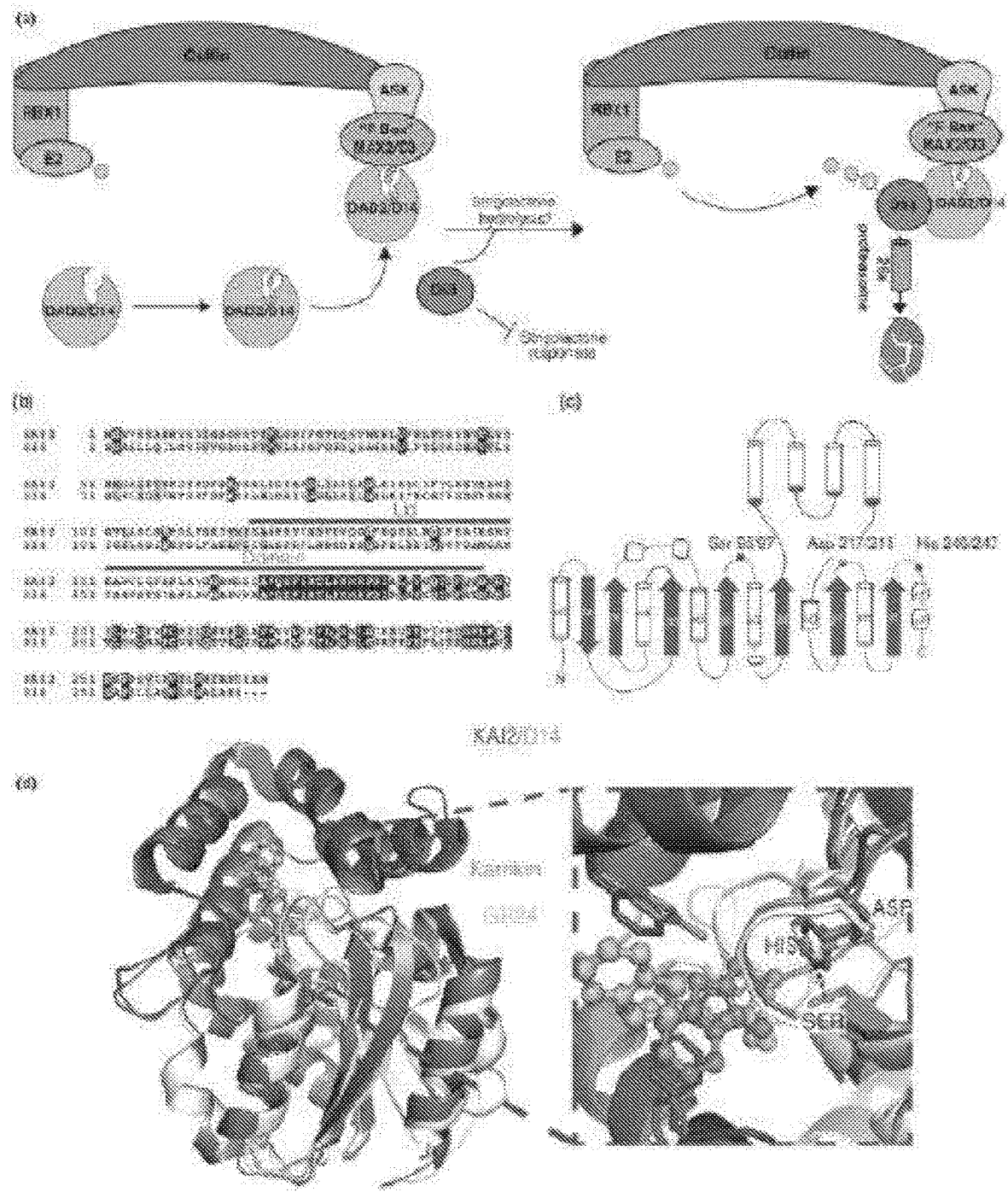

METHODS FOR CONTROLLING ROOT PARASITIC WEEDS: INHIBITORS OF SEED GERMINATION IN STRIGA

CROSS-REFERENCE TO RELATED APPLICATIONS

This application is a National Phase application under 35 U.S.C. 371 of PCT/IB2018/052425, filed Apr. 6, 2018, which claims priority to and benefit of U.S. Patent Application No. 62/484,173 filed Apr. 11, 2017, and U.S. Patent Application No. 62/641,491 filed Mar. 12, 2018, which are incorporated by reference herein in their entirety.

TECHNICAL FIELD

The presently-disclosed invention relates generally to inhibiting root parasitic plant growth, and more particularly to herbicides, systems, and methods for inhibiting germination of root parasitic plants without affecting germination of host plants.

BACKGROUND

Root parasitic plants of the Orobanchaceae family cause severe yield losses in different crops, including cereals, legumes, sunflowers and different Solanaceae species. Seeds of these plants persist in the soil for very long time and germinate only after perceiving chemical signals from host plants, ensuring the survival of the germinating parasite. The germination signals are usually strigolactones, a group of carotenoid-derived plant hormones that are also released by plant roots into the soil. However, plants do not release strigolactones into soil to attract parasites but rather to invite mycorrhizal fungi to establish the known beneficial mycorrhizal symbiosis. Emerging seedlings of root parasitic plants develop the so called haustorium that connects them to the roots of the host plant, enabling to siphon water, minerals and sugars from the host. Root parasitic weeds have different host specificities. For instance, *Striga* species like *S. asiatica, S. aspera, S. forbesii*, and particularly *S. hermonthica* infest cereals, such as sorghum, maize, millet and rice, while *S. gesnerioides* attacks cowpea and other legumes. In the Middle East, India and large parts of Europe, Orobanche and Phelipanche species infest dicotyledonous crops including tomato, tobacco, carrot, clovers, cucumber, sunflower and legumes. These weeds are widely spread, threatening around 16 million hectares of farmland in the Mediterranean and West Asia. *Striga* parasitism is one of the seven most severe threats to food security, leading to enormous yield losses in many parts of the world. However, it is difficult to prevent germination of *Striga* without harming host plant germination.

Accordingly, there exists a need for inhibiting seed germination in *Striga* while permitting seed germination in host plants.

BRIEF SUMMARY OF THE INVENTION

One or more embodiments of the invention may address one or more of the aforementioned problems. Certain embodiments provide herbicides, systems, and methods for inhibiting germination of a root parasitic plant. In one aspect, an herbicide for inhibiting germination of a root parasitic plant is provided. The herbicide may include an active compound represented by Formula I:

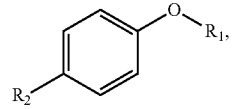

such that $R_1$ is selected from the group consisting of:

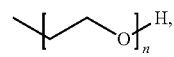

a carboxyl group, and an acyl group, wherein when $R_1$ is the carboxyl group or the acyl group, $R_1$ optionally includes a straight chain $C_1$-$C_n$ alkyl group between O and the carboxyl group or the acyl group; $R_2$ is a straight chain or branched $C_6$-$C_{10}$ alkyl group; and n is from 1 to 40. The active compound may be selected to bind to an active site of at least one strigolactone receptor in seeds of the root parasitic plant.

In another aspect, a system for inhibiting germination of a root parasitic plant is provided. The system may include an herbicide and a host plant. The herbicide may include an active compound represented by Formula I:

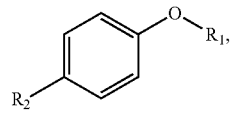

such that $R_1$ is selected from the group consisting of:

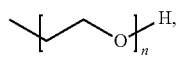

a carboxyl group, and an acyl group, wherein when $R_1$ is the carboxyl group or the acyl group, $R_1$ optionally includes a straight chain $C_1$-$C_n$ alkyl group between O and the carboxyl group or the acyl group; $R_2$ is a straight chain or branched $C_6$-$C_{10}$ alkyl group; and n is from 1 to 40. The active compound of the herbicide may be selected to bind to an active site of at least one strigolactone receptor in seeds of the root parasitic plant without affecting germination of the host plant.

In yet another aspect, a method for inhibiting germination of a root parasitic plant is provided. The method may include applying an herbicide to a planting area for a host plant before seed germination of the root parasitic plant. The herbicide may include an active compound represented by Formula I:

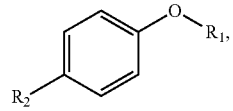

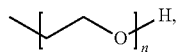

such that $R_1$ is selected from the group consisting of: a carboxyl group, and an acyl group, wherein when $R_1$ is the carboxyl group or the acyl group, $R_1$ optionally includes a straight chain $C_1$-$C_n$ alkyl group between O and the carboxyl group or the acyl group; $R_2$ is a straight chain or branched $C_6$-$C_{10}$ alkyl group; and n is from 1 to 40. The active compound of the herbicide may be selected to bind to an active site of at least one strigolactone receptor in seeds of the root parasitic plant without affecting germination of the host plant.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

FIG. 1 illustrates various structures of strigolactones;

FIG. 2 illustrates the life cycle of root parasitic plants;

FIG. 3 illustrates how strigolactones shape the architecture of plants;

FIG. 4 illustrates the structural and functional homology of strigolactones and karrikin receptors;

FIG. 5 illustrates the crystal structure of the *Striga* strigolactone receptor ShHTL7 bound to a polyethylene glycol tert-octylphenyl ether;

FIG. 6 illustrates that the polyethylene glycol tert-octylphenyl ether binds specifically to ShHTL7 and blocks strigolactone binding sites, in accordance with certain embodiments of the invention;

FIG. 7 illustrates the electron density of polyethylene glycol tert-octylphenyl ether in an ShHTL7 bound structure and cysteine converted to sulfinic acid in an S95C mutant, in accordance with certain embodiments of the invention;

FIG. 8 illustrates how a polyethylene glycol tert-octylphenyl ether binds tightly to ShHTL7 and inhibits substrate hydrolysis, in accordance with certain embodiments of the invention;

FIGS. 9A and 9B illustrate how polyethylene glycol tert-octylphenyl ether specifically inhibits *Striga* germination but does not affect the host plant rice, in accordance with certain embodiments of the invention;

FIG. 10 illustrates the sequence alignment of ShHTLs and homologs from non-parasitic plants, in accordance with certain embodiments of the invention; and FIG. 11 illustrates superimposition of ShHTL7, ShHTL5, Rice D14, and *Arabidopsis* D14, in accordance with certain embodiments of the invention.

DETAILED DESCRIPTION

The invention now will be described more fully hereinafter with reference to the accompanying drawings, in which some, but not all embodiments of the inventions are shown. Indeed, this inventions may be embodied in many different forms and should not be construed as limited to the embodiments set forth herein; rather, these embodiments are provided so that this disclosure will satisfy applicable legal requirements. Like numbers refer to like elements throughout. As used in the specification, and in the appended claims, the singular forms "a", "an", "the", include plural referents unless the context clearly dictates otherwise.

Plants in the *Striga* genus are root parasitic plants that infest, for example, cereals, threating food security worldwide, and particularly in Sub-Saharan Africa, the Middle East, India, and Europe. For germination, *Striga* seeds require host-released strigolactones ("SLs") that are perceived by HYPOSENSITIVE to LIGHT ("ShHTL") receptors. Efficacious control of *Striga* would need specific herbicides, such as SL antagonists that block ShHTLs but not the homologous host plant receptor DWARF14 ("D14").

FIG. 2, for example, illustrates the life cycle of root parasitic plants such as *Striga*. As shown in FIG. 2*a*, seeds of root parasitic plants germinate only after perceiving host-derived germination stimulants, such as SLs. FIG. 2*b* shows that seedlings develop radicle and then haustoria that attach to host roots. FIGS. 2*c*-2*d* illustrates the several weeks of growth it takes until the parasites appear above the soil. Finally, FIG. 2*e* illustrates that after flowering, root parasitic plants produce large numbers of seeds that remain viable for many years in soil.

FIG. 3 illustrates how SLs shape the architecture of plants. In particular, SLs (a) determine the length of internodes, (b) mediate leaf senescence, (c) trigger the elongation of root hairs and the growth of primary roots, (d) induce enhanced secondary growth, (e) inhibit the outgrowth of axillary buds (e.g., reduce the number of shoot branches), (f) inhibit the formation of adventitious roots, and (g) inhibit the formation of lateral roots.

Canonical SLs include a tricyclic lactone (ABC-ring) moiety that is connected via an enol ether bridge to a further lactone (D-ring). Based on the stereochemistry of the B/C junction, they are divided into the orobanchol and strigol-like family. In addition, there are non-canonical SLs, such as carlactone-like SLs, that vary in the moiety corresponding to the ABC-ring, i.e. non-canonical SLs lack one of the A, B, or C rings but have the enol ether D-ring moiety. Modifications of the ABC ring in canonical SLs and the presence of different structures that replace the ABC-ring in non-canonical SLs give rise to the diversity of natural SLs, some of which are illustrated in FIG. 1.

Apart from their role in inducing seeds germination of root parasitic weeds, SLs are plant hormones that shape the architecture of plants in accordance with the availability of minerals, such as phosphate. In addition, SLs are involved in the response of plants to abiotic stress. SLs are perceived by $\alpha/\beta$ hydrolase (D14 in rice) that hydrolyze these compounds leading to a covalent binding of the D-ring with the receptor. This process is accompanied by conformational changes and leads to the proteasome-mediated degradation of target proteins such as D53 in rice, which is supposed to inhibit the expression of SLs' inducible genes. The receptor itself is also subjected to degradation. In *Arabidopsis*, this process is mediated by the F-box protein More axillary growth 2 (MAX2; D3 in rice), a component of a Skp1-Cullin-F-box (SCF) E3 ubiquitin ligase complex that catalyzes the polyubiquitination of specific protein substrates, which are then degraded by the 26S proteasome. D14 acts as both a SL receptor and enzyme. The enzymatic activity is mediated by a conserved Ser-His-Asp catalytic triad that is needed for SL hydrolysis and also for the signaling function. Binding of the SL analog GR24 leads to thermal destabilization of the receptor, which requires the presence of the catalytic triad. The crystal structure of the *Arabidopsis* perception complex shows that the D14 protein forms an intermediate structure in which the D-ring—released due to the hydrolysis of SLs—is covalently bound to the His residue of the catalytic triad. This modification leads to a closed-state conformation with a small binding pocket.

The protein KARRIKIN-INSENSITIVE2 (KAI2)/HYPOSENSITIVE to LIGHT (HTL)/D14-like is a close homolog to D14. However, KAI2 and D14 have different ligand specificity, as shown in FIG. 4. KAI2 mediates the response of plants to karrikin, a compound that arises by wood brand and which is known to trigger seed germination in "normal" (non-parasitic) plants. It is believed that karrikin mimics an unidentified plant hormone. In addition, KAI2 binds synthetic SLs with an S-configuration that is usually not present in natural SLs. D14 and KAI are evolutionary related, they share the same F-box protein (MAX2 in *Arabidopsis*) to transduce their signals, and are structurally very similar, however D14 has a larger ligand-binding pocket.

The root parasitic weed *Striga hermonthica*, for example, has 12 SLs receptor candidates (named ShHTL1 to ShHTL11 and ShD14) with homology to AtD14 and AtKAI2. Functional tests of their activity revealed that ShHTL2 to 11 can hydrolyze the synthetic SLs GR24 and Yushimolactone Green (YLG), a fluorogenic agonist for D14. Functional complementation of the *Arabidopsis* kai2 mutant shows that ShHTL7 is a functional SL receptor that induces germination in *Arabidopsis*. Moreover, testing of different SLs in transformed *Arabidopsis* plants shows that ShHTL7 is 100 times more sensitive than the other ten SL receptors.

Through applied effort, ingenuity, and innovation, the inventors have identified a family of active compounds that potently inhibit *Striga* seed germination without affecting the host plant. High-resolution X-ray structures reveal that these active compounds plug the deep catalytic pocket of, for example, ShHTL7, the most sensitive ShHTL. Structural and functional analyses explain the specificity of these active compounds. In this regard, the inventors have identified a way for combating *Striga* by blocking seed germination without harming the host plant.

I. Herbicide for Inhibiting Germination of a Root Parasitic Plant

In accordance with certain embodiments of the invention, an herbicide for inhibiting germination of a root parasitic plant is provided. In one embodiment, the herbicide comprises a carrier and a p-disubstituted phenyl ether having a straight chain or branched $C_6$-$C_{10}$ alkyl group, and a polyethylene oxide chain, carboxyl group, or acyl group attached to the ether. In certain embodiments, the herbicide includes a carrier and an active compound represented by Formula I:

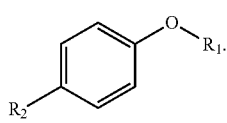

(I)

In Formula I, $R_1$ is selected from the group consisting of a carboxyl group, an acyl group, and

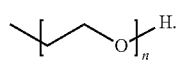

In some exemplary embodiments in which $R_1$ is a carboxyl group or an acyl group, for example, $R_1$ may further include a carbon chain between the ether O and the carboxyl group or the acyl group. For instance, in certain embodiments, the carbon chain may comprise a $C_1$ to $C_n$ alkyl group. In further embodiments, $R_2$ is a straight chain or branched $C_6$-$C_{10}$ alkyl group. In some embodiments, for example, $R_2$ may be a tert-octyl group. In other embodiments, for instance, $R_2$ may be a branched nonyl group ($C_9H_{19}$) as shown below:

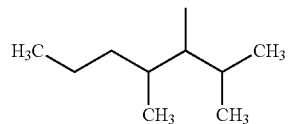

According to certain embodiments, for example, n is from 1 to 40. In other embodiments, for instance, n is from 5 to 20. In further embodiments, for example, n is from 8 to 16. In this regard, the active compound is selected to bind to an active site of at least one strigolactone receptor (e.g., ShHTL receptors) in seeds of the root parasitic plant.

According to certain embodiments, the active compound may comprise (but is not limited to) at least one or any combination of:

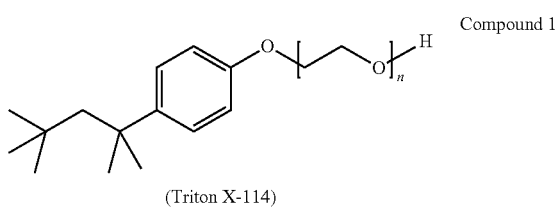

(Triton X-114)
n = 7-8

Compound 1

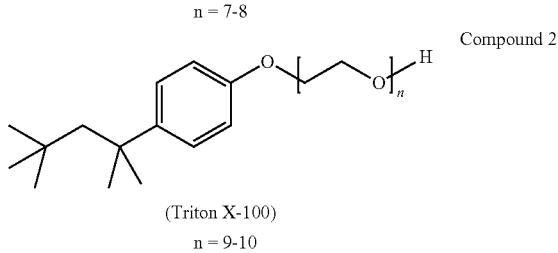

(Triton X-100)
n = 9-10

Compound 2

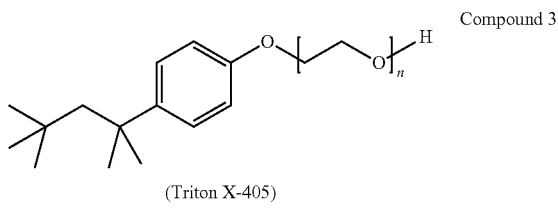

(Triton X-405)
n = 40

Compound 3

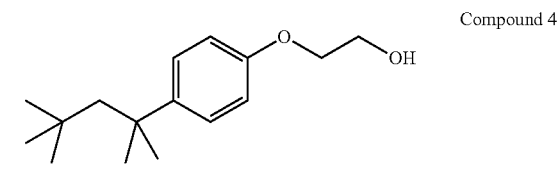

(4-tert-octylphenol monoethoxylate)

Compound 4

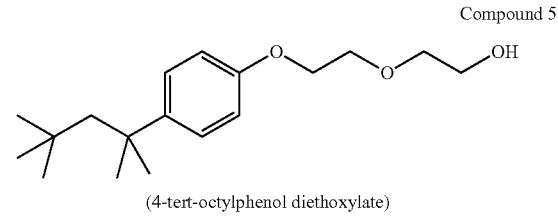

(4-tert-octylphenol diethoxylate)

Compound 5

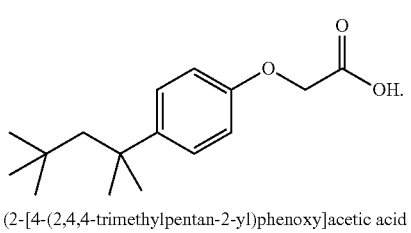

Compound 6

(2-[4-(2,4,4-trimethylpentan-2-yl)phenoxy]acetic acid

These compounds are nonionic surfactants having a hydrophilic polyethylene oxide chain and an aromatic hydrocarbon lipophilic or hydrophobic group. These compounds bind to ShHTL (e.g., ShHTL7) receptors by positioning the hydrophobic moiety entirely inside the active site pocket of the receptor. Such binding results from strong, covalent interactions including, but not limited to, hydrophobic interactions, hydrogen bonds, van der Waals forces, and the like.

According to certain embodiments, for example, the herbicide may comprise the active compound and a carrier. In some embodiments, for instance, the herbicide may comprise the active compound at a concentration of about 1 to about 100 μM. In certain embodiments, the carrier may comprise an aqueous solution. In other embodiments, for instance, the carrier may be formulated with emulsifiers. In further embodiments, for example, the carrier may comprise nanoparticles. For example, the carrier may comprise at least one of water, liquid fertilizer (e.g., liquid urea-ammonium nitrate fertilizer (UAN)), petroleum, plant oils, dry fertilizer, clay, lime, vermiculite, ground corn cob, attapulgite (i.e. palygorskite), kaolinite, bentonite, starch polymers, and/or the like as understood by one of ordinary skill in the art.

According to certain embodiments, the herbicide may be produced in any suitable formulation as understood by one of ordinary skill in the art (e.g., powder, spray, coating, etc.). For example, the herbicide may comprise at least one of an emulsifiable concentrate, and emulsifiable gel, a wettable powder, a soluble liquid, a soluble powder, a dry flowable, a flowable, a suspension concentrate, an aqueous suspension, a microencapsulated suspension, a capsule suspension, granules, pellets, and/or the like as understood by one of ordinary skill in the art. In some embodiments, the active compound and the carrier may be similarly formed so as to be suitable for the desired formulation of the herbicide as understood by one of ordinary skill in the art.

According to certain embodiments, for example, the root parasitic plant may comprise at least one species from the family Orobanchaceae. In this regard, the root parasitic plant may be from one of any of the following genera: *Aeginetia, Agalinis gerardia, Alectra, Asepalum Aureolaria, Bartsia, Bellardia, Boschniakia, Brandisia, Buchnera, Bungea, Buttonia, Castilleja, Centranthera, Christisonia, Cistance, Clevelandia, Conopholis, Cordylanthus, Cycnium, Cymbaria, Dasistoma, Epifagus, Escobedia, Eremitilla, Esterhazya, Euphrasia, Gerardina, Ghikaea, Gleadovia, Graderia, Harveya, Hedvergia, Hyobanche, Lamourouxia, Lathraea, Leptorhabdos, Leucosalpa, Lindenbergia, Macranthera, Magdalenaea, Mannagettaea, Melampyrum, Melasma, Micrargeria, Micrargeriella, Monochasma, Nesogenes, nothobarsia, Nothochilus, Odontites, Omphalotrix, Ophiocephalus, Orobanche, Orthocarpus, Parastriga, Parentucellia, Pedicularis, Petitmenginia, Phacellanthus, Phelypaea, Phtheirospermum, Physocalyx, Platypholis, Pseudobartsia, Pseudomelasma, Pseudosopubia, Pseudostriga, Pterygiella, Radamaea, Rehmannia, Rhamphicarpa, Rhaphispermum, Rhinanthus, Rhynchocorys, Schwalbea, Seymeria, Sieversandreas, Silviella, Siphonostegia, Sopubia, Spirostegia, Striga, Tetraspidium, Thunbergianthus, Tienmuia, Tozzia, Triaenophora, Triphysaria, Vellosiella, Xizangia,* and *Xylocalyx.*

In particular, in some embodiments, for instance, the root parasitic plant may comprise at least one *Striga* species. In this regard, the root parasitic plant may comprise, for example, one of the following species: *Striga asiatica, Striga gesnerioides, Striga hermonthica, Striga aequinoctialis, Striga angolensis, Striga angustifolia, Striga aspera, Strica bilabiata, Striga brachylcalyx, Striga chrysantha, Striga dalzielii, Striga elegans, Striga forbesii, Striga gastonii, Striga gracillima, Striga hallaei, Striga hirsute, Striga indica, Striga junodii, Striga klingii, Striga latericea, Striga lepidagathidis, Striga lutea* (a synonym for *Striga asiatica*), *Striga macrantha, Striga passargei, Striga pinnatifida, Striga primuloides, Striga pubiflora,* and *Striga yemenica.* In particular, in certain embodiments, for instance, the root parasitic plant may comprise at least one of *Striga asiatica, Striga aspera, Striga forbesii, Striga hermonthica, Striga* gesnerioides, or any combination thereof.

In this regard, according to certain embodiments, for example, the herbicide may selectively inhibit *Striga* seed germination. In further embodiments, for instance, the herbicide may comprise a *Striga*-specific agonist.

II. System for Inhibiting Germination of a Root Parasitic Plant

In another aspect, systems for inhibiting germination of a root parasitic plant are provided. The system includes the herbicide described in detail above and a host plant. In this regard, the active compound of the herbicide may be selected to bind to an active site of at least one strigolactone receptor (e.g., ShHTL receptors) in seeds of the root parasitic plant without affecting germination of the host plant.

In some embodiments, for example, the host plant may comprise at least one of a monocotyledonous crop, a dicotyledonous crop, or any combination thereof. Monocotyledonous crops may be any monocotyledonous plant harvested as a food source including, but not limited to, a cereal, sugarcane, etc. A cereal, for example, may be any grass cultivated for the edible components of its grain, which includes the endosperm, germ, and bran. Examples of cereals may include, but are not limited to, rice, wheat (e.g., einkorn, durum, kamut, etc.), millet, maize, sorghum, barley, rye, spelt, oats, triticale, fonio, teff, wild rice, and/or the like. Dicotyledonous crops may be any dicotyledonous plant harvested as a food source. Examples of dicotyledonous crops may include, but are not limited to, legumes, broccoli, cauliflower, turnips, cabbage, carrots, celery, parsley, rosemary, sage, thyme, apples, peaches, pears, plums, potatoes, tomatoes, peppers, tobacco, cucumber, sunflowers, and/or the like. Examples of legumes may include, but are not limited to, alfalfa, clover, peas, beans (e.g., kidney bean, lima bean, mung bean, broad bean, etc.), cowpeas (i.e. black-eyed peas), chickpeas, lentils, lupin beans, mesquite, carob, soybeans, peanuts, tamarind, and/or the like.

III. Method for Inhibiting Germination of a Root Parasitic Plant

In yet another aspect, methods for inhibiting germination of a root parasitic plant are provided. The method includes applying the herbicide described in detail above to a planting area for a host plant before seed germination of the root parasitic plant. In some embodiments, for example, the herbicide may be applied to the planting area for the host plant during planting season of the host plant. In other embodiments, for instance, the herbicide may be applied to the planting area of the host plant before planting season. In either scenario, the herbicide may be applied to the planting area such that the host plant will be able to grow, but the seeds of the root parasitic plant will not germinate.

EXAMPLES

The following examples are provided for illustrating one or more embodiments of the present invention and should not be construed as limiting the invention.

Testing Methods and Materials

Protein Cloning, Expression, and Purification cDNA fragments, encoding the *S. hermonthica* ShHTL7 or the mutated version S95C (in which the serine in the active triad was changed to cysteine) flanked with BamHI and XhoI restriction sites, were cloned into the pGEX-6P1 (GE Healthcare) expression vector that enables the expression of GST fusion protein, using the corresponding restriction sites, as shown in Table 1 below. The plasmid obtained was then transformed into BL21 (DE3) *E. coli* cells. Cells were grown in LB medium at 37° C., and protein expression was induced at OD 0.6 at λ=600 nm by adding 150 µM isopropyl β-D-1-thiogalactopyranoside (IPTG). After induction, cultures were grown at 16° C. overnight under shaking. Cultures were then harvested, and pellets corresponding to 1 liter culture were re-suspended in 25 ml lysis buffer (50 mM Tris-HCl [pH 8.0], 200 mM NaCl, 3 mM DTT, 0.5% Triton X-100 or 0.5% Tween 20), followed by sonification. After centrifugation at 30,000 g for 30 min, supernatant was isolated, and the protein was purified using Glutathione Sepharose 4B resins (GE Healthcare). The GST tag was then removed by overnight incubation with Prescission Protease (GE healthcare) at 4° C. Proteins were further purified on a HiLoad16/60 Superdex 200 prep-grade gel filtration column (GE Healthcare) in a buffer containing 10 mM HEPES (pH 7.5), 50 mM KCl, 3 mM DTT. The purified protein was concentrated to 10 mg/ml and stored at −80° C.

Crystallization and Structure Determination

For crystallization, the hanging drop vapor diffusion method was used. Initial plate crystals were obtained by equilibrating 1.0 µl of protein (15 mg/ml) mixed with 1.0 µl of reservoir solution (0.2 M Magnesium Chloride, 0.1 M Tris-HCl pH 8.5 and 30% PEG 4000). The produced crystals were crushed and used as microseeds to obtain diffraction quality crystals under the same crystallization conditions. For ShHTL7 with Triton X-100, diffraction-quality crystals were obtained by equilibrating 1.0 µl of protein (10 mg/ml) mixed with 1.0 µl of reservoir solution (1 M Lithium Sulfate, 0.1 M HEPES pH 7.5). All crystals grew in 1-3 days at 23° C. For data collection, 25% glycerol was added to the well solution as a cryo-protectant and the crystals were flash-cooled in liquid nitrogen. Data were collected at 100K, at the beamline Proxima 1, SOLEIL Synchrotron (France), using a Pilatus 6M detector and processed with XDS. The structure was determined by molecular replacement using MoRDa with using the ShHTL5 structure as a search model. The structures were manually inspected and rebuilt using Coot and refined using Phenix (Table X-ray Statistics).

Yoshimulactone Green (YLG) Hydrolysis Analysis

For measuring the hydrolysis of YLG in vitro, 10 µg of purified ShHTL7, AtD14 and OsD14 in a reaction buffer (1×PBS) containing 0.1% dimethyl sulfoxide (DMSO) in a total volume of 100 µL in 96-well black plate (Greiner) were used. To measure the fluorescent intensity, SpectraMax i3 (Molecular Devices) with an excitation wavelength of 480 nm and a detection wavelength of 520 nm were used. Purified proteins were mixed with Triton X-100, using serial dilutions with concentrations ranging from 5 µM to 4.87 nM. Proteins were pre-incubated with Tritone X-100 for 30 min, followed by incubation with 1 µM YLG (Tokyo Chemical Industry Co. Ltd., product number E1238) for 60 min. Fluorescence values measured in the void control were subtracted from those obtained in the presence of protein. Curves and $IC_{50}$ values were plotted using Graph pad (PRISM 6) four-parameter logistic curve.

Triton X-100 Fluorescence

Purified proteins (at concentrations of 1 nm to 5 µM) were incubated with 1.54 µM of Triton X-100 for 2 h. Since Triton X-100 has an excitation and emission wavelength of 275 nm and 302 nm, fluorescence was measured at the corresponding wavelengths using SpectraMax i3 (Molecular Devices). The fluorescence exhibited by Triton X-100 alone was subtracted from the fluorescence in the presence of protein.

TABLE 1

Primers sequences used for protein cloning

| Primer name | Sequence (5'-3') | Restriction site |
|---|---|---|
| ShHTL7-F | CGggatccATGAGCTCAATTGGATTAGCCC | BamHI |
| ShHTL7-F | CCGctcgagTCAGTGATCCGTGATGTCCTG | XhoI |
| AtD14-F | CGgaattcATGAGTCAACACAACATCTTAGAAG | EcoRI |
| AtD14-R | ACGCgtcgacTCACCGAGGAAGAGCTCG | SalI |
| OsD14-F | CGggatccATGCTGCGATCGACGCATCC | BamHI |
| OsD14-R | CCGctcgagTTAGTACCGGGCGAGAGCGC | XhoI |
| ShHTL7-S95C-F | CGggatccATGAGCTCAATTGGATTAGCCC | BamHI |
| ShHTL7-S95C-R | CCGctcgagTCAGTGATCCGTGATGTCCTG | XhoI |
| ShHTL7-L143Y-F | GAGCAGAAGGTGATGGATGAGACGTACAGGTCCTTGGACGAGAAC | |
| ShHTL7-L143Y-R | GTTCTCGTCCAAGGACCTGTACGTCTCATCCATCACCTTCTGCTC | |

Data were normalized to the background fluorescence from the protein and values obtained in absence of proteins were subtracted, to determine changes in Triton X-100 fluorescence intensity. $K_d$ values were determined by plotting changes in Triton X-100 fluorescence intensity against the concentration of the protein, using the single binding site model implemented in Graph pad (PRISM 6).

Differential Static Light Scattering (DSLS)

The specific aggregation temperature, $T_{agg}$, was determined using DSLS on the Stargazer system (Harbinger Biotechnology and Engineering Corporation, Markham, Canada). For this purpose, purified protein (1 mg/mL) was overlaid with mineral oil in a clear bottom 384-well black plate (Corning), and temperature was increased from 20 to 95° C. with a ratio of 1° C./min. A CCD camera was used to detect light scattering every 0.5° C. in the presence or absence of varying concentrations of Triton X-100, unraveling X-100 concentration-dependent changes in aggregation temperature (ShHTL7 $\Delta T_{agg}$). Data were normalized, and $\Delta T_{agg}$ was plotted against the Triton X-100 concentration. Resulting data were plotted to determine the change in $T_{agg}$ of ShHTL7 upon binding to Triton X-100 using Graph pad (PRISM 6).

Striga hermonthica Germination Assay

Striga hermonthica germination bioassays were carried out using Striga seeds collected from a Sorghum bicolor field in Sudan. About 50-100 dry Striga washed and sterilized seeds were distributed on a 9-mm diameter glass fiber filter paper discs (Sartorius, Goettingen Germany). Discs were then placed in 9-cm diameter petri-dishes (12 discs per petri-dish) on filter paper (Whatman, Maidstone, UK) moistened with 3 mL sterilized water. The petri-dishes were sealed with parafilm, wrapped with aluminum foil and incubated in growth chambers at 30° C. for 10 days for preconditioning. On the 11$^{th}$ day, discs were air dried in laminar flow cabinet and transferred to 9-cm petri-dishes (four discs in each plate), which contained 9-mm diameter glass fiber filter paper rings, moistened with 900 μL sterile MilliQ water. The pre-conditioned Striga seeds were treated with Triton X-100 at concentrations of 15.4 μM (0.001%) and 1.54 μM (0.0001%) along with GR24 at 1 nM, 0.5 nM, 0.25 nM and 0.125 nM respectively. Triton X-100/GR24 mixtures were applied (50 μl per disc) in four replicates. Corresponding volumes of GR24 and sterile MilliQ water were included as positive and negative control, respectively. The petri-dishes were sealed with parafilm, enfolded with aluminum foil and incubated for 48 h at 30° C. The germinated (seeds with radicle emerging through the seed coat) and non-germinated Striga seeds were recorded under a binocular and germination percentage was calculated.

Rice Seed Germination Assay and Seedling Growth

The rice seeds cv. Nipponbare were surface-sterilized using 50 ml (2.5%) sodium hypochlorite with 0.4% of Tween-20 for 15 min. After six subsequent washing steps with sterilized water, the rice seeds were kept in water at 30° C. for overnight imbibition. About 2 ml of dilutions of Triton X-100 at 15.4 μM, 1.54 μM in sterile MilliQ water (control) was added in 24-well plates with six replications. One sterilized rice seed was put in each well and allowed to germinate for 48 h at 30° C. The germinated (radicle emergence) and non-germinated seeds were recorded and germination percentage was calculated. Then same seeds were allowed to grow under light in growth cabinet for another one week. The length of one week old seedlings was measured with a roller and averaged.

Example 1

Figure 5:
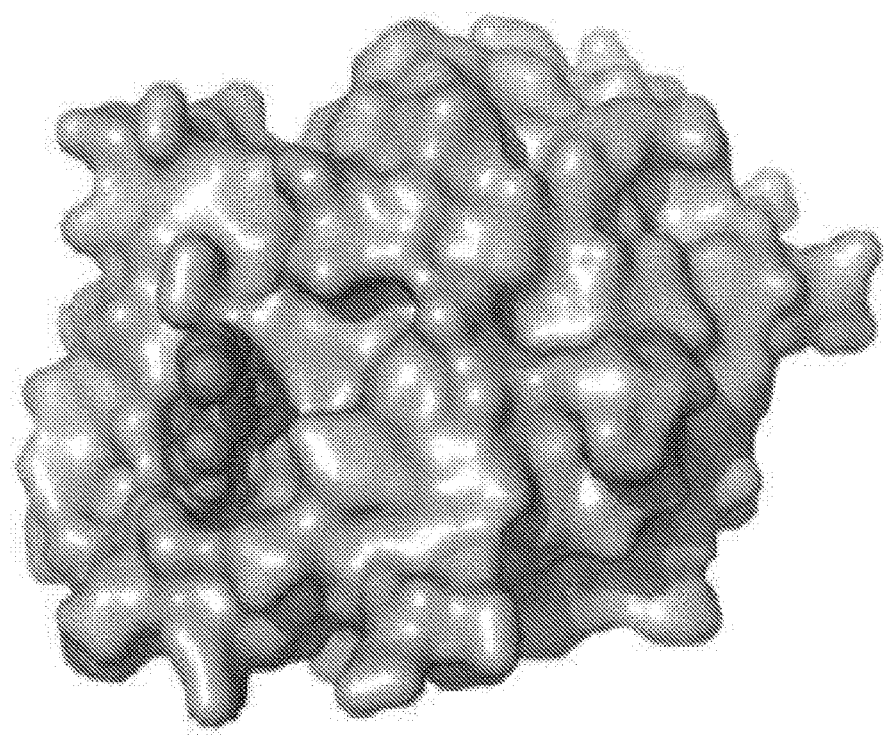
Figure 5:
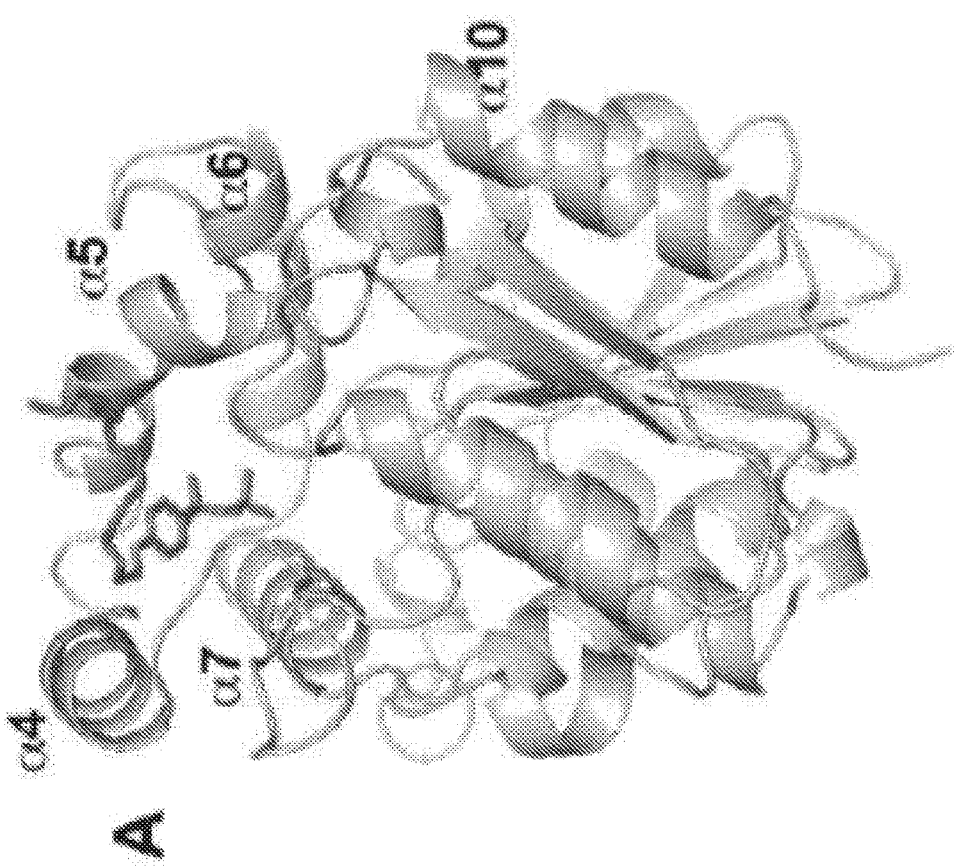
Figure 6:
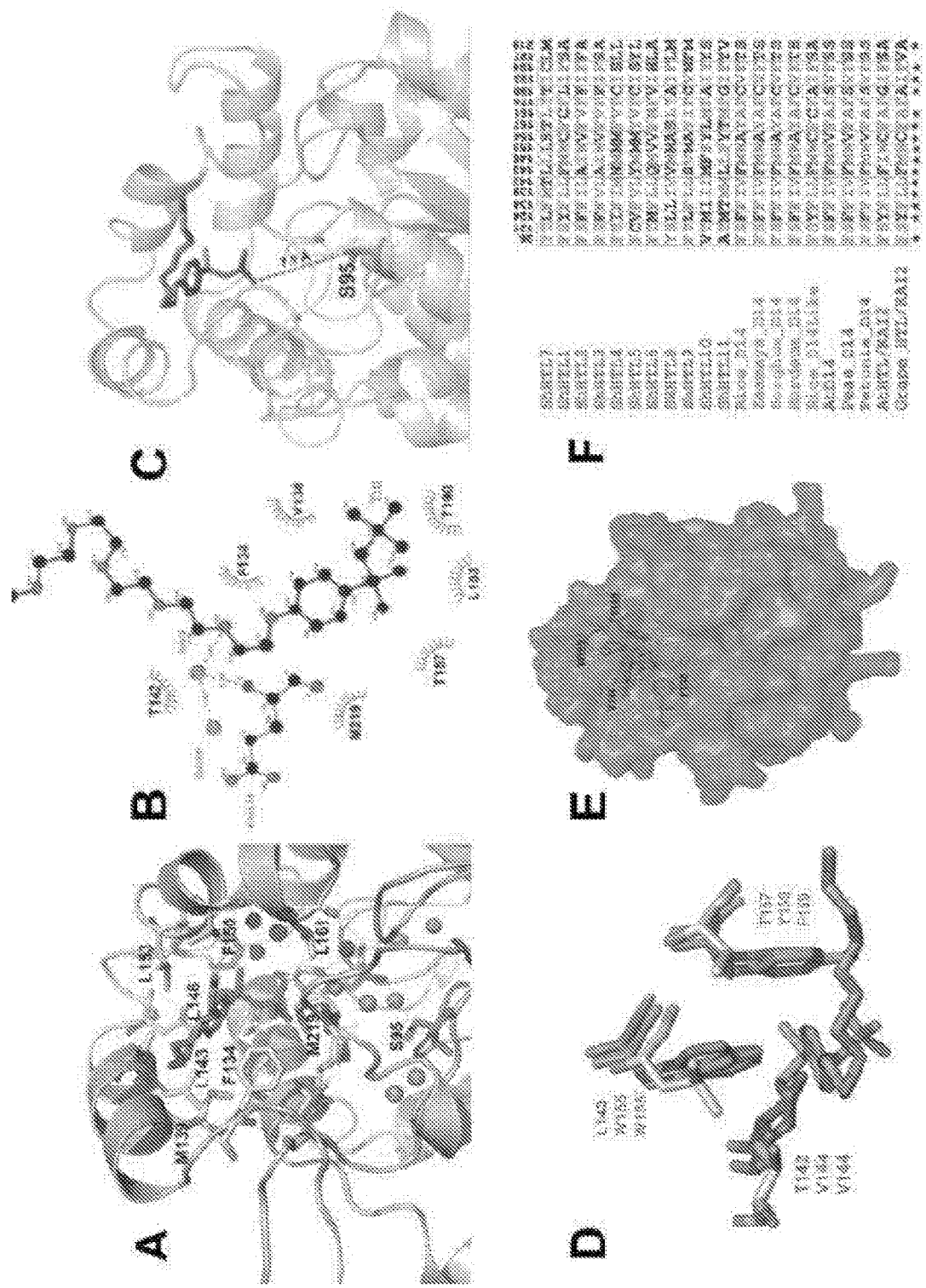

X-ray crystallography was used to obtain high-resolution (1.2 to 1.7 Å) diffraction patterns of wild-type and active site mutant (S95C) ShHTL7 proteins, summarized by the data shown in Table 2 below. The phase problem was solved using molecular replacement methods. The 2FoFc electron density showed a small molecule compound bound in the ShHTL7 active site. Owing to the high-resolution of the data, this bound molecule could clearly be identified as Triton X-100 (hereafter referred to as Triton, unless stated otherwise), as illustrated in FIG. 5. Interestingly, Triton was only used briefly in the recombinant protein purification protocol, during Escherichia coli cell lysis. Triton was absent in all crystal structures of ShHTL7 when omitted from the purification protocol, confirming the origin and nature of this compound. Triton bound to the active site pocket that is built by helices α4-α5 and α6-α7, which form a stacked double V-like cavity, as shown in FIG. 5. The 4-(1,1,3,3-tetramethylbutyl)-phenyl hydrocarbon group is the main source of interactions with ShHTL7. This hydrophobic moiety is positioned entirely inside the active site pocket and has many hydrophobic interactions with ShHTL7, namely with Y26 (loop following β2), L124, F134 (β5-a4 loop), M139, T142, L143, L146 (on a4), F150 (a4-a5 loop), L153, T157, L161 (a5), T190, I193, C194 (a7), and M219 (β6-a8 loop), as shown in FIG. 6. All five ethylene oxide units that are defined in the electron density reach out of the active site pocket. This polyethylene oxide is only weakly bound to the rim of the binding pocket. Interactions are established through hydrophobic contacts (between carbons of the first unit and a hydrophobic pocket formed by V138, M139 and T142, and between carbons of the fourth unit and L160 and I218) and a water-mediated hydrogen bond from the first oxide to the backbone nitrogen of E135. Without being bound by theory, this particular position of the polyethylene oxide in the crystal may be influenced by the proximity of a symmetry-related molecule, especially its residues I106 and F107.

TABLE 2

| | X-Ray Statistics | | |
| --- | --- | --- | --- |
| Crystal | ShHTL7_WT_Apo | ShHTL7_WT_Triton | ShHTL7_S95C_Triton |
| Resolution range Å | 45.28-1.7 (1.761-1.7) | 40.09-1.2 (1.243-1.2) | 19.45-1.423 (1.474-1.423) |
| Space group | I 2 2 2 | P 65 | P 65 |
| Cell Dimensions a, b, c, Å | 73.98 84.04 90.55 | 92.59 92.59 80.26 | 92.57 92.57 80.19 |
| No. of Unique reflections measured | 31351 (3061) | 121689 (12066) | 72852 (7139) |
| Redundancy | 9.8 (7.9) | 9.9 (9.6) | 14.4 (13.8) |
| Completeness (%) | 99.80 (98.61) | 99.98 (99.95) | 99.72 (97.66) |
| Mean I/σ (I) | 12.05 (1.04) | 24.56 (1.87) | 30.40 (4.52) |
| R-merge | 0.1034 (1.482) | 0.04276 (1.069) | 0.05644 (0.76) |

TABLE 2-continued

X-Ray Statistics

| Crystal | ShHTL7_WT_Apo | ShHTL7_WT_Triton | ShHTL7_S95C_Triton |
|---|---|---|---|
| R-pim | 0.03445 (0.5538) | 0.0142 (0.3641) | 0.01533 (0.2128) |
| CC1/2 | 0.998 (0.449) | 1 (0.721) | 1 (0.886) |
| Refinement | | | |
| Resolution range Å | 45.28-1.7 (1.761-1.7) | 40.09-1.2 (1.243-1.2) | 19.45-1.423 (1.474-1.423) |
| Reflections used in refinement | 31351 (3060) | 121689 (12061) | 72852 (7138) |
| Reflections used for R-free | 1571 (156) | 6083 (603) | 3642 (356) |
| R-work | 0.2082 | 0.1236 | 0.1007 |
| R-free | 0.2360 | 0.1374 | 0.1201 |
| No. of atoms in Protein | 2087 | 2270 | 2232 |
| No. of atoms in ligands | 8 | 41 | 47 |
| No. of atoms in solvent | 178 | 325 | 301 |

Figure 7:
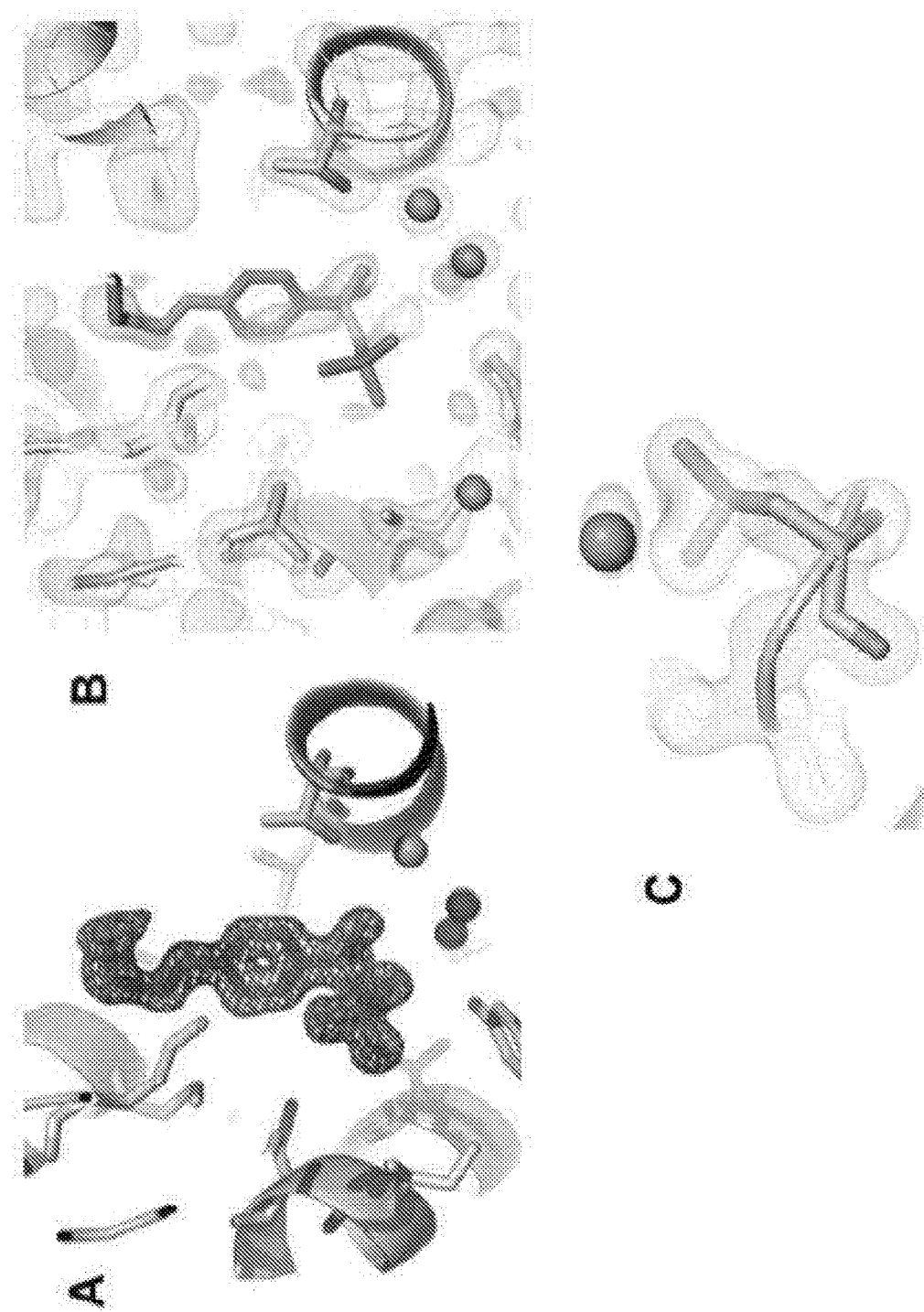

Although Triton bound to the active site pocket, its binding site is different from that of SLs. The polyethylene oxide moiety is more than 8 Å away from the catalytic serine S95, and hence fails to reach the active site. Consequently, Triton physically blocks the active site entrance without being in contact with the catalytic residues, as shown in FIG. 6. Ten well-ordered water molecules fill the gap between Triton and the bottom of the active site pocket. This water network is well-preserved in crystals grown in absence of Triton, hence, Triton did not need to disrupt it for binding. The Triton density was consistently better defined in the crystals formed by the S95C mutant as compared to wild-type ShHTL7. Since the occupancy of Triton did not vary between wild-type and C95, this effect suggests a higher mobility (but not lesser occupancy) of Triton in the mutant. The cause for the increased flexibility of Triton in the wild-type structure is unclear, because the mutation only led to a minor rearrangement of the H94 side chain in otherwise identical structures (RMSD of 0.108 Å). This rearrangement occurred to compensate in ShHTL7S95C for an unusual modification that oxidized C95 into a sulfinic acid, as shown in FIG. 7.

Example 2

Figure 8:
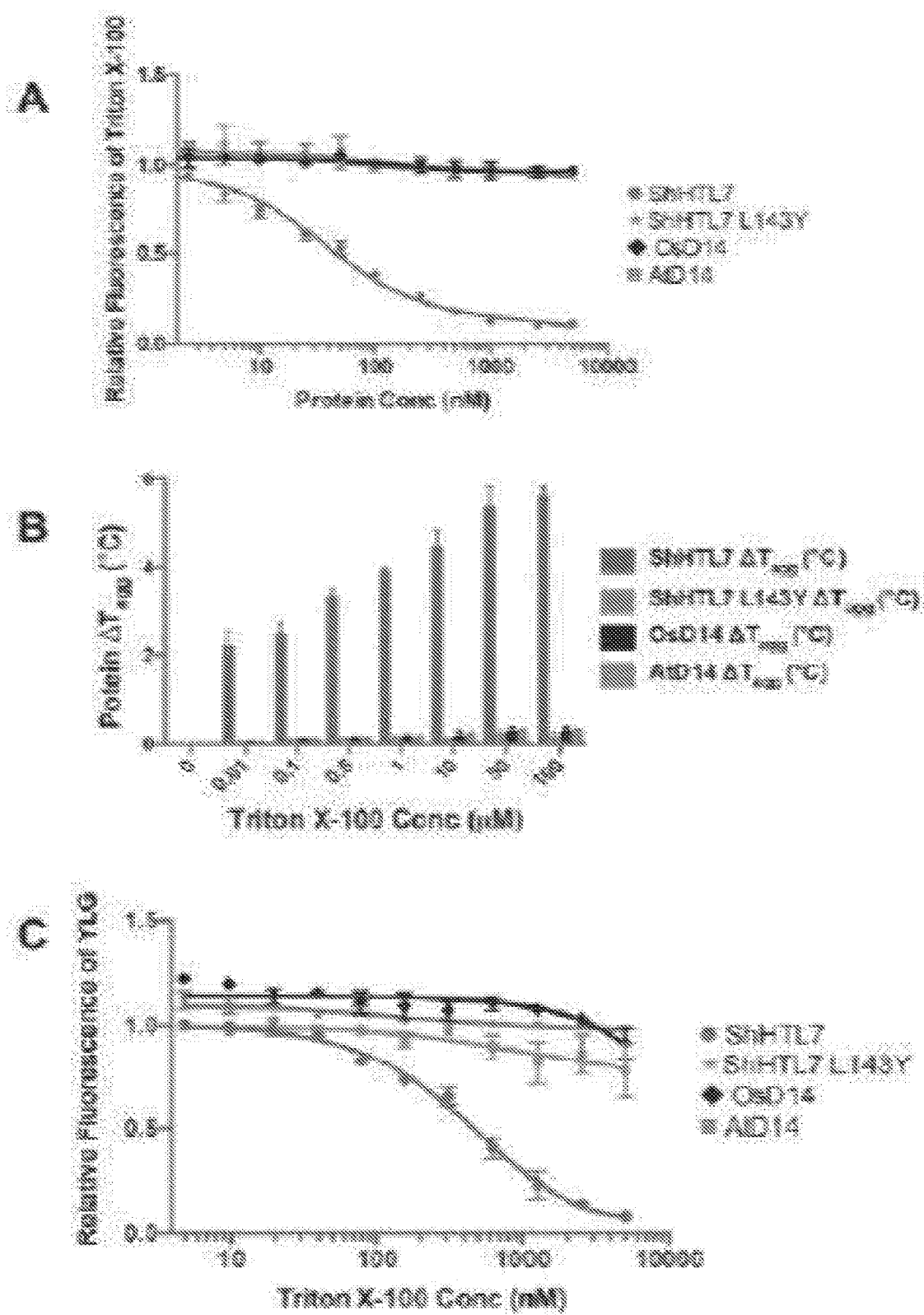

Triton bound ShHTL7 specifically with high potency in vitro. Triton remained associated with ShHTL7 despite washes, dialyses and size exclusion columns with buffers without Triton, and despite extensive exposure to high concentrations of the synthetic SL GR24. Therefore, the association of Triton with ShHTL7 was expected to be very strong. A high affinity between Triton and ShHTL7 was apparent in assays where ShHTL7 was pre-incubated with Triton for 2 h or more, akin to the time of Triton treatment during cell lysis, as shown in FIG. 8. Following pre-incubation, a $K_d$ of 31 nM between Triton and ShHTL7 was measured using intrinsic Triton fluorescence assays, the results of which are shown in FIG. 8A. Triton's association with ShHTL7 had about ten times higher affinity than that of ShHTL7 and GR24 ($K_d$ of 440 nM). Following pre-incubation, a tight Triton-ShHTL7 association was also apparent in aggregation temperature increases in a Triton concentration-dependent manner, as shown in FIG. 8B, providing a complementary qualitative confirmation of direct binding.

These experiments suggested that Triton can inhibit SL binding and hydrolysis by blocking the active site access. In agreement, pre-incubation with Triton blocked Yoshimulactone green (YLG) hydrolysis by ShHTL7 with an $IC_{50}$ of 0.47±0.11 µM, as shown in FIG. 8. Hence, Triton is a potent SL hydrolysis inhibitor in vitro.

Example 3

Figure 9A:
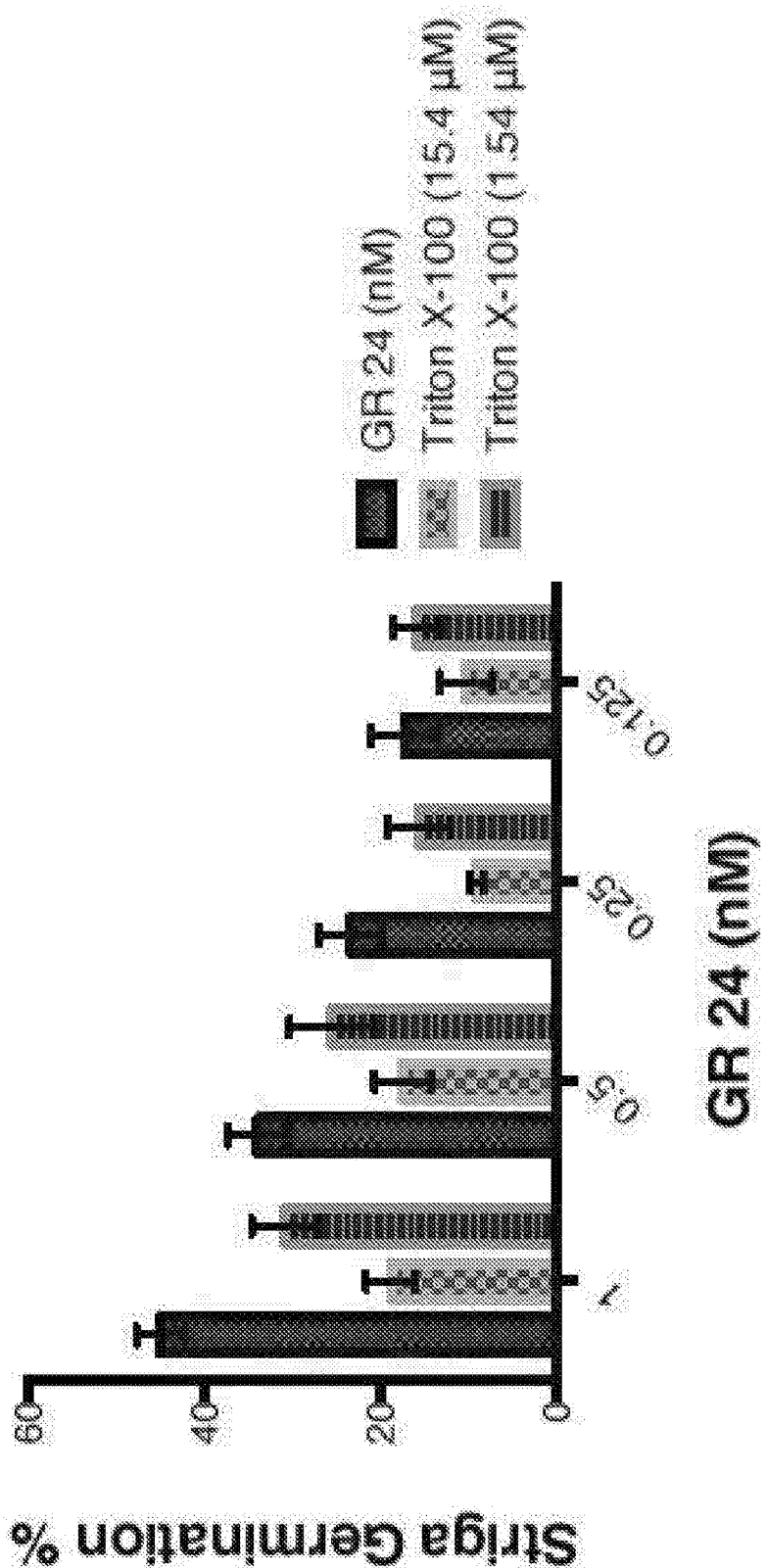

Germination bioassays were used to assess the potency of Triton in plants. Striga hermonthica seeds were prepared as discussed previously herein. Triton also revealed to be a potent germination inhibitor in vivo, with both 1.54 µM and 15.4 µM Triton X-100 significantly inhibiting GR24-induced S. hermonthica germination, as shown in FIG. 9A. S. hermonthica genome encodes for eleven HTL proteins. It has been shown that in A. thaliana lines transformed with different ShHTL cDNAs, the expression of ShHTL7 can trigger germination when exposed to picomolar concentrations of GR24 while other ShHTL proteins (ShHTL4, 5, 6, 8 and 9) were much less sensitive, displaying $EC_{50}$ values of 0.01 to 0.15 µM for GR24. Thus, in principle, S. hermonthica germination in presence of 1 µM GR24 might be triggered by ShHTLs other than ShHTL7. To evaluate the likelihood of Triton to inhibit not only ShHTL7 but also other family members, structural homology models based on ShHT7 and ShHTL5 were built and analyzed. This computational analysis strongly suggested that ShHTL4, 5, 6, 8 or 9 cannot all bind Triton with high (nanomolar) affinities. Especially, the active site composition of ShHTL5 and 6 appeared to preclude Triton binding. For ShHTL5, Triton binding is unlikely because T157Y causes steric clashes, L143Y may preclude open helix3 positioning, and L153M appears suboptimal. For ShHTL6, Triton binding is unlikely because C194H and T157Y cause steric clashes, and the polar nature of C194H is unfavorable in this position, which is in close contact with the hydrophobic tail of Triton. M219A deletes an important hydrophobic contact and adds an opening in the binding site. Taken together, the strong in vivo germination inhibition by Triton indicates that ShHTL7 is the master regulator of Striga germination.

Example 4

Figure 9B:
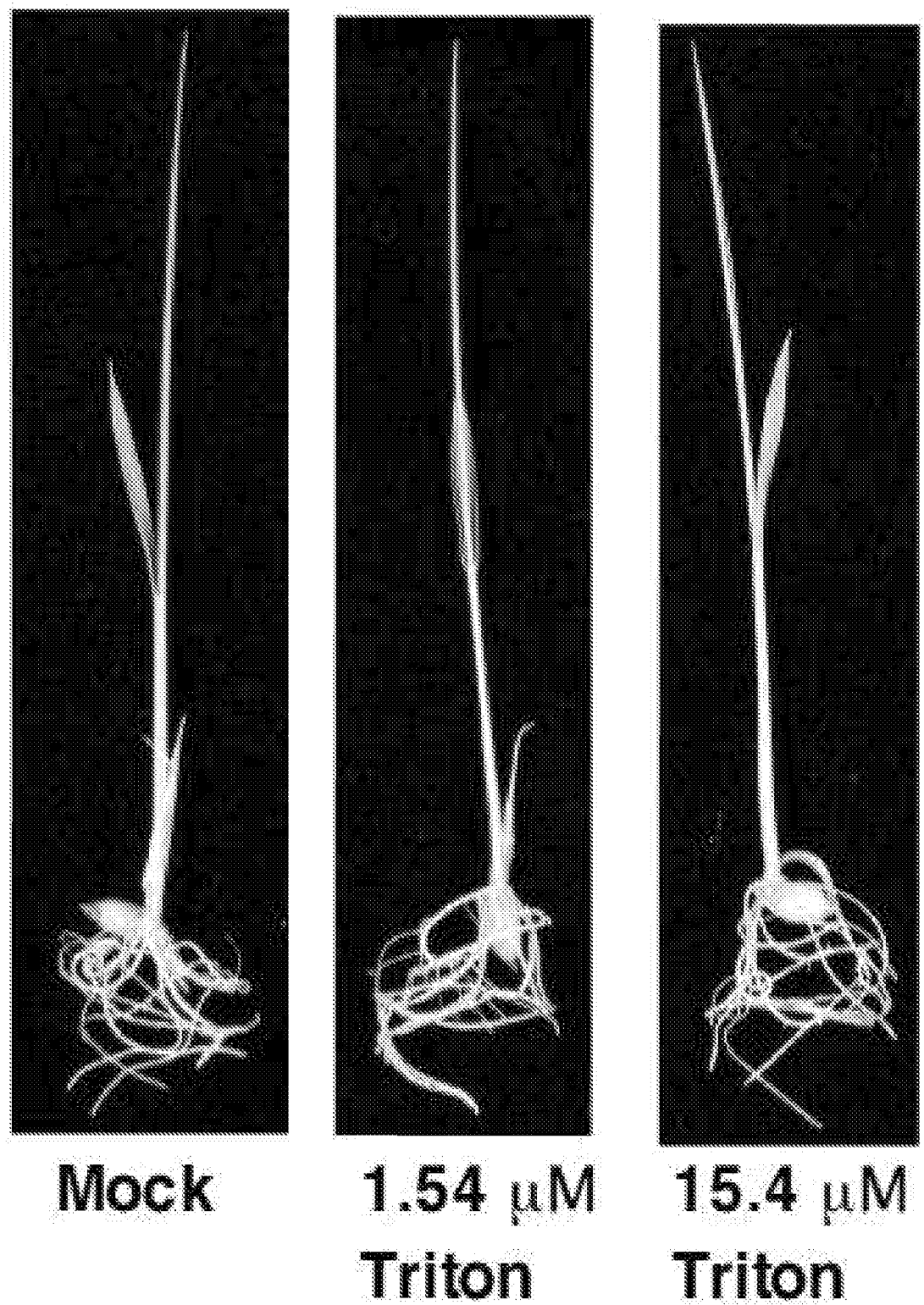

SLs exert various important functions in plants. To be useful as an inhibitor of Striga, it has to be assured that Triton does not compete with SLs or bind to the corresponding receptor in non-parasitic plants. Triton fluorescence assays were used to assess binding of Triton in vitro to the ShHTL orthologue D14 from A. thaliana (AtD14) and rice (OsD14). No change in Triton fluorescence was observed for AtD14 and OsD14 concentrations up to 10 µM, excluding strong direct association between Triton and AtD14 or OsD14, as shown in FIG. 8. Up to 0.5 µM, Triton did not affect YLG hydrolysis by AtD14 or OsD14, and even 10 µM Triton showed only weak inhibition (around 10%) of the YLG hydrolysis, as shown in FIG. 8. Rice germination was not affected by up to 15.4 µM Triton, as no inhibition of rice seed germination or growth retarding effects on treated seedlings was observed, as shown in FIG. 9B. These results suggested that Triton can be used as a specific inhibitor of *Striga* germination at concentrations that do not impact the germination and growth of host plants.

Example 5

Figure 10:
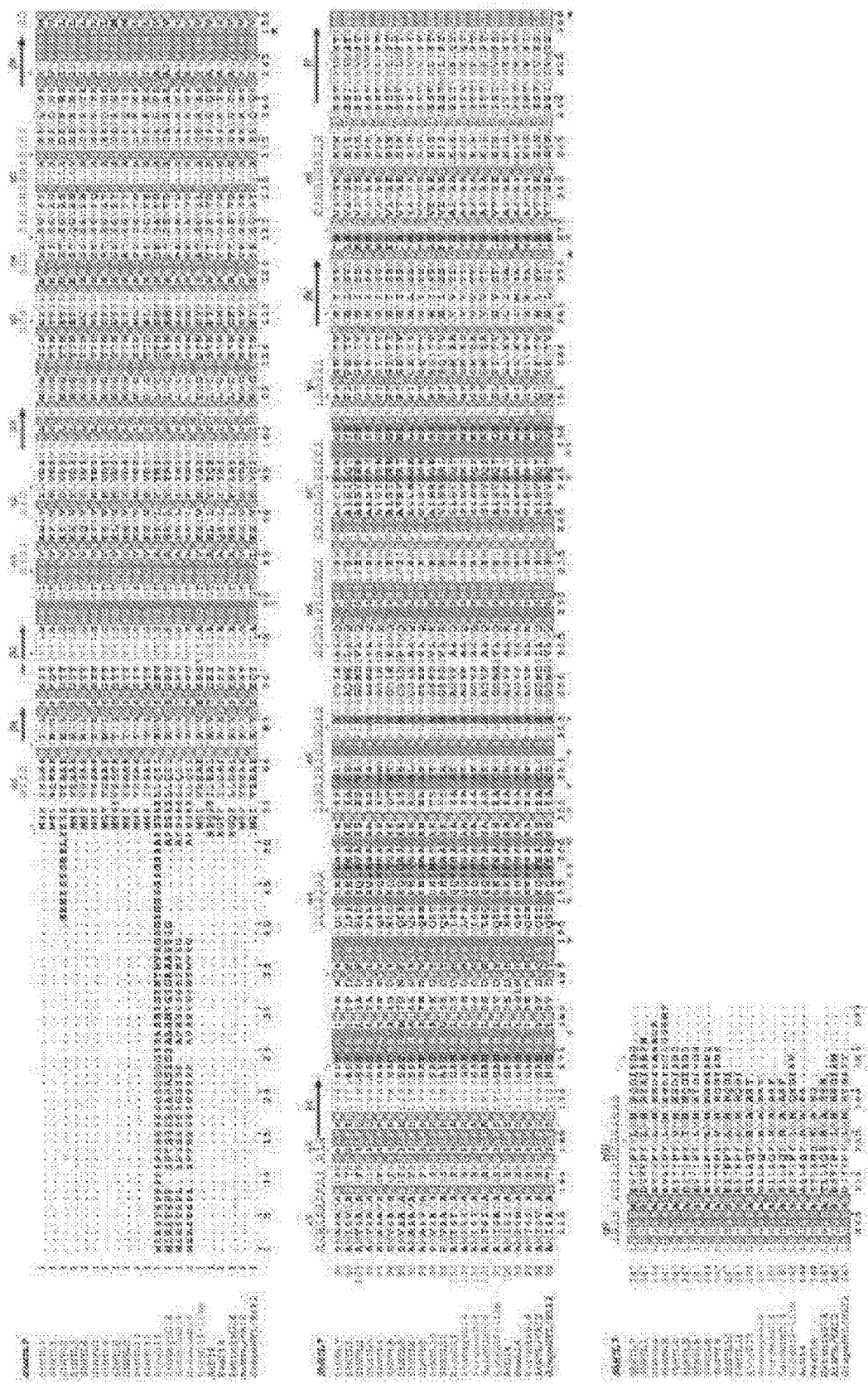
Figure 11:
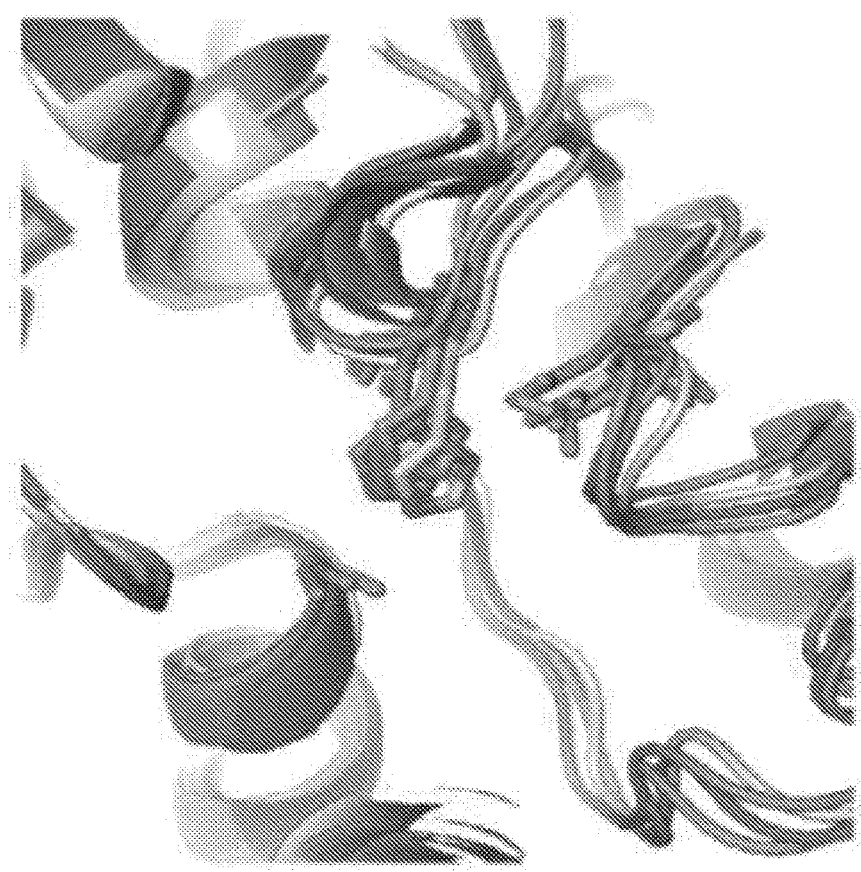
Figure 11:
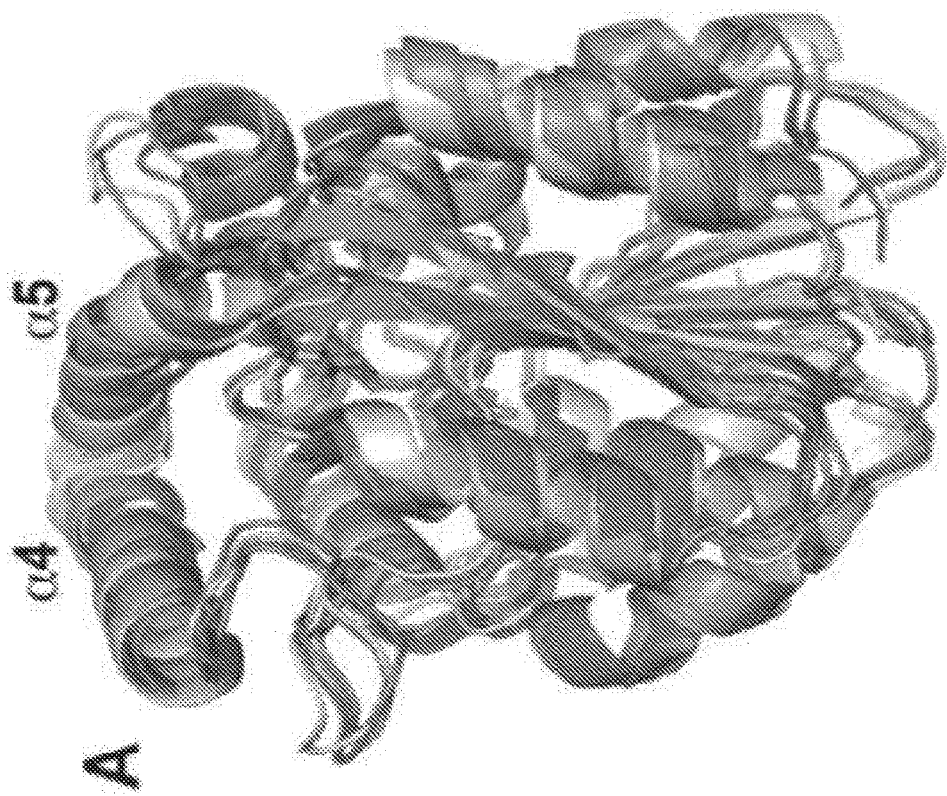

To determine why Triton does not inhibit AtD14 and OsD14 catalyzed hydrolysis of YLG, the structure of ShHTL7 was compared with the elucidated structures of AtD14, OsD14 and ShHTL5, as shown in FIGS. 10 and 11. The secondary structure elements of ShHTL5, ShHTL7, AtD14, and OsD14 superimpose very closely (RMSD of 1.12 Å). Significant changes occur mainly in helices a4 and a5 of the active site pocket entrance. The opening between a4 and a5 is smallest in AtD14 and OsD14. The a3-a4 opening in ShHTL5 is larger resulting in an active site pocket entrance backbone widened by about 1.5 Å. This ShHTL5 a4-a5 opening is still ~2 Å narrower than the Triton-bound P65 form of ShHTL7, shown in FIG. 11. Computational structural analyses suggested that the particularly large opening of a4 is only possible for ShHTL7. In ShHTL5 or any of the other non-*Striga* orthologues, the replacement of ShHTL7 L143 by tyrosine (ShHTL5) or phenylalanine (all other homologs) was expected to hamper the sliding of a4 over a7. In agreement, Triton failed to inhibit YLG hydrolysis by the ShHTL7 L143Y mutant, as shown in FIG. 8C. In addition, even if all orthologues could adapt a ShHTL7-like open form, the substitution of several small to medium sized side chains in the ShHTL7 binding pocket with bulky side chains in non-*Striga* KAI2/D14 (L153W, T157F/Y, C194F) would still block Triton binding. These substitutions would lead to a reduction in the size of the binding pocket that cannot be tolerated by Triton.

Example 6

Triton X-114 (with 7-8 polyethylene repeats, compared to 9-10 in Triton X-100) and 2-[4-(2,4,4-trimethylpentan-2-yl) phenoxy]acetic acid that carries a phenoxy acid group instead of the polyethylene repeats were tested to determine whether they also inhibited the ShHTL7 catalyzed hydrolysis of YLG. Though with a higher $IC_{50}$ than Triton X-100, as shown in Table 3 below, both compounds showed a clear inhibitory effect on the ShHTL7 activity. The activity of other Tritons—with 1, 2, 5 or 40 polyethylene repeats—was significantly weaker. These results identified the head moiety (polyethylene repeats) as a significant modulator of binding strength, suggesting that careful rational choice of functional groups in this position can provide derivatives with increased affinity over Triton X-100, which can be used as *Striga* germination inhibitor. The high-resolution structure of Triton-bound ShHTL7 also suggests that derivatives with modified tail groups (hydrophobic moiety) may exploit the gap between Triton and the active site and occupy a larger space in the active pocket.

TABLE 3

IC50 Values of triton X-100 like compounds

| No. of ethylene oxide Groups | Compound | IC50 (µM) |
|---|---|---|
| 40 | Triton X-405 | 11.52 ± 2.8 |
| 9-10 | Triton X-100 | 0.47 ± 0.11 |
| 7-8 | Triton X-110 | 2.15 ± 0.5 |
| 2 | 4-ter-octylphenol diethoxylate | 7.5 ± 2.1 |
| 1 | 4-ter-octylphenol Monoethoxylate | 9.2 ± 3.2 |
| None (Phenoxy acetic acid) | 2-[4-(2,4,4-trimethylpentan-2-yl)phenoxy]acetic acid | 1.5 ± 0.41 |

In this regard, Triton X-100 is a highly potent and selective inhibitor of seed germination in *Striga*. By binding to the active site of ShHTL7, Triton X-100 inhibits *S. hermonthica* germination up to 90%. Importantly, *S. hermonthica* germination is inhibited substantially by Triton concentrations that are five orders of magnitude lower than concentrations that affect rice growth. The results showed that inhibition of ShHTL7 is sufficient for suppression of GR24-induced germination, despite GR24 binding to other ShHTL family members. This effect is expected to be preserved and even strengthened in natural soil where SL concentrations are substantially lower than 1 µM. ShHTL7 is by far the most responsive HTL family member for relevant natural SLs, strongly suggesting a broad inhibitory effect of Triton in a natural setting. Triton has several advantages compared to current synthetic SL mimics, including affordable synthesis and extremely high specificity. Structural analyses allow rationalization of this specificity as being promoted by particular ShHTL7 features such as its unique capacity for helix a4 opening and its uniquely large binding pocket.

Non-Limiting Exemplary Embodiments

Having described various aspects and embodiments of the invention herein, further specific embodiments of the invention include those set forth in the following paragraphs.

Certain embodiments provide herbicides, systems, and methods for inhibiting germination of a root parasitic plant. In one aspect, an herbicide for inhibiting germination of a root parasitic plant is provided. The herbicide may include an active compound represented by Formula I:

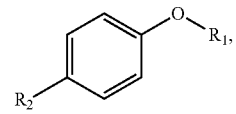

such that $R_1$ is selected from the group consisting of:

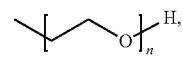

a carboxyl group, and an acyl group, wherein when $R_1$ is the carboxyl group or the acyl group, $R_1$ optionally includes a straight chain $C_1$-$C_n$ alkyl group between O and the carboxyl group or the acyl group; $R_2$ is a straight chain or branched $C_6$-$C_{10}$ alkyl group; and n is from 1 to 40. The active compound may be selected to bind to an active site of at least one strigolactone receptor in seeds of the root parasitic plant.

According to certain embodiments, for example, the active compound may comprise at least one of:

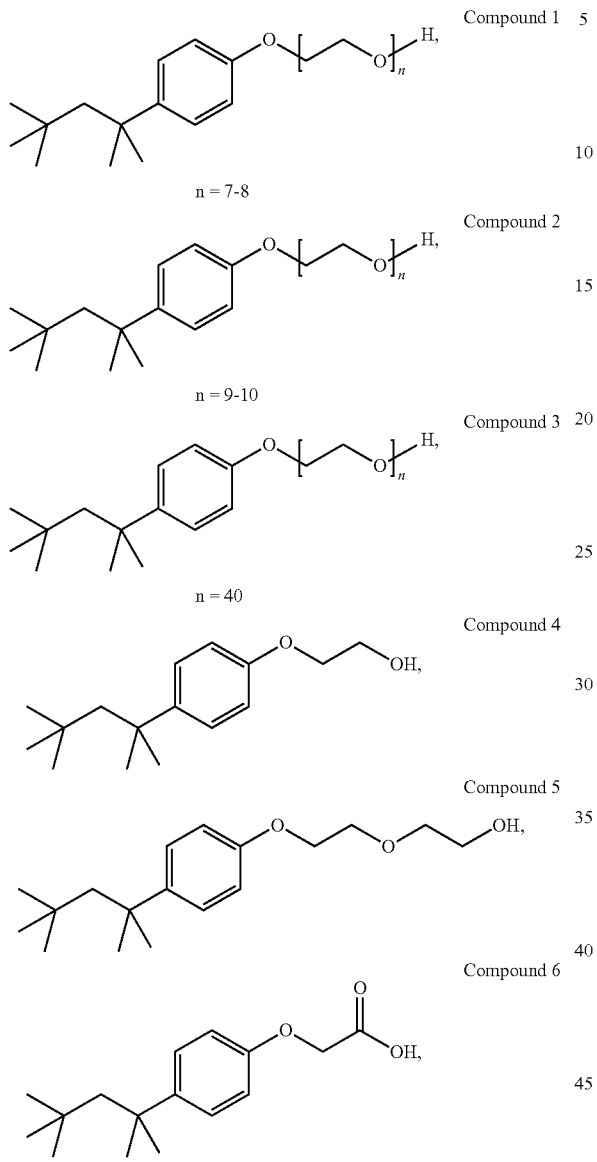

or any combination thereof. In some embodiments, for example, the herbicide may further comprise a carrier.

In accordance with certain embodiments, for instance, the root parasitic plant may comprise at least one *Orobanchaceae* species. In some embodiments, for example, the root parasitic plant may comprise at least one *Striga* species. In further embodiments, for instance, the root parasitic plant may comprise at least one of *Striga asiatica, Striga aspera, Striga forbesii, Striga hermonthica, Striga gesnerioides*, or any combination thereof.

In accordance with certain embodiments, for example, the herbicide may selectively inhibit *Striga* seed germination. In some embodiments, for instance, the herbicide may comprise a *Striga*-specific agonist. In further embodiments, for example, the at least one strigolactone receptor may comprise an ShHTL7 receptor. In such embodiments, for instance, the active compound may be selected to bind to an active site of the ShHTL7 receptor in seeds of the root parasitic plant.

In another aspect, a system for inhibiting germination of a root parasitic plant is provided. The system may include an herbicide and a host plant. The herbicide may include an active compound represented by Formula I:

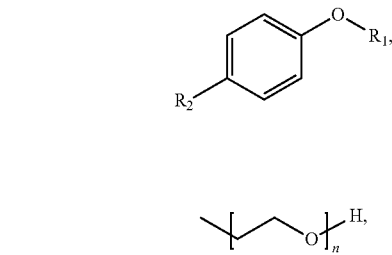

such that $R_1$ is selected from the group consisting of: a carboxyl group, and an acyl group, wherein when $R_1$ is the carboxyl group or the acyl group, $R_1$ optionally includes a straight chain $C_1$-$C_n$ alkyl group between O and the carboxyl group or the acyl group; $R_2$ is a straight chain or branched $C_6$-$C_{10}$ alkyl group; and n is from 1 to 40. The active compound of the herbicide may be selected to bind to an active site of at least one strigolactone receptor in seeds of the root parasitic plant without affecting germination of the host plant. According to certain embodiments, for example, the active compound may comprise at least one of:

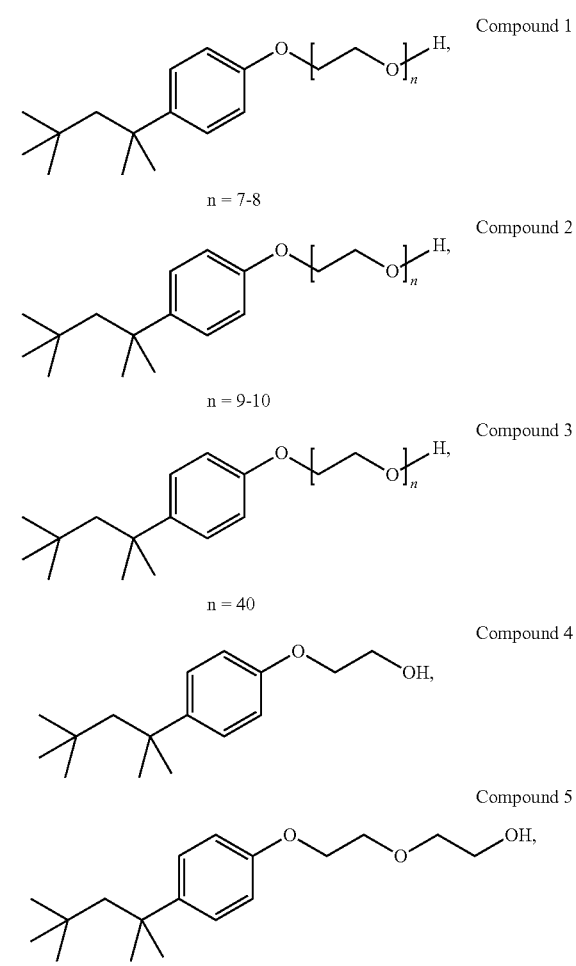

-continued

Compound 6

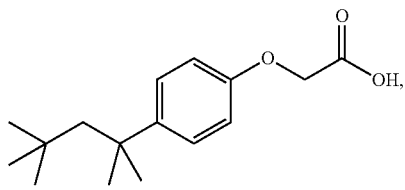

or any combination thereof. In some embodiments, for example, the herbicide may further comprise a carrier.

In accordance with certain embodiments, for instance, the root parasitic plant may comprise at least one *Orobanchaceae* species. In some embodiments, for example, the root parasitic plant may comprise at least one *Striga* species. In further embodiments, for instance, the root parasitic plant may comprise at least one of *Striga asiatica, Striga aspera, Striga forbesii, Striga hermonthica, Striga gesnerioides,* or any combination thereof.

In accordance with certain embodiments, for example, the herbicide may selectively inhibit *Striga* seed germination. In some embodiments, for instance, the herbicide may comprise a *Striga*-specific agonist. In further embodiments, for example, the at least one strigolactone receptor may comprise an ShHTL7 receptor. In such embodiments, for instance, the active compound may be selected to bind to an active site of the ShHTL7 receptor in seeds of the root parasitic plant.

In accordance with certain embodiments, for example, the host plant may comprise at least one of a monocotyledonous crop, a dicotyledonous crop, or any combination thereof. In some embodiments, for instance, the host plant may comprise at least one of sorghum, maize, millet, rice, cowpea, tomato, tobacco, carrot, clover, cucumber, sunflower, or any combination thereof.

In yet another aspect, a method for inhibiting germination of a root parasitic plant is provided. The method may include applying an herbicide to a planting area for a host plant before seed germination of the root parasitic plant. The herbicide may include an active compound represented by Formula I:

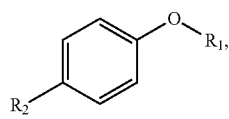

such that $R_1$ is selected from the group consisting of:

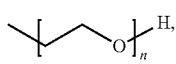

a carboxyl group, and an acyl group, wherein when $R_1$ is the carboxyl group or the acyl group, $R_1$ optionally includes a straight chain $C_1$-$C_n$ alkyl group between O and the carboxyl group or the acyl group; $R_2$ is a straight chain or branched $C_6$-$C_{10}$ alkyl group; and n is from 1 to 40. The active compound of the herbicide may be selected to bind to an active site of at least one strigolactone receptor in seeds of the root parasitic plant without affecting germination of the host plant. According to certain embodiments, for example, the active compound may comprise at least one of:

Compound 1

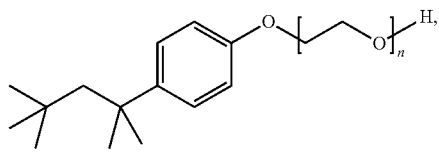

n = 7-8

Compound 2

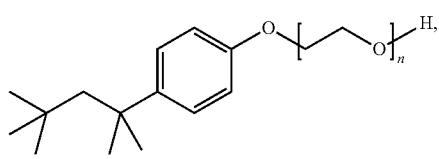

n = 9-10

Compound 3

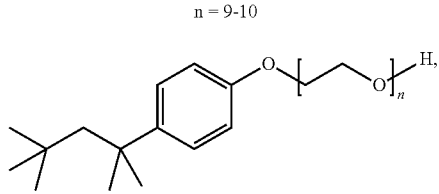

n = 40

Compound 4

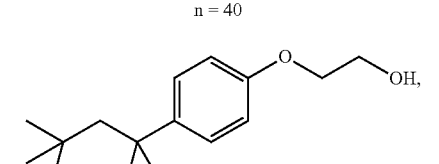

Compound 5

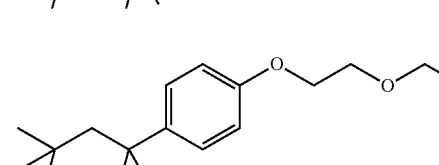

Compound 6

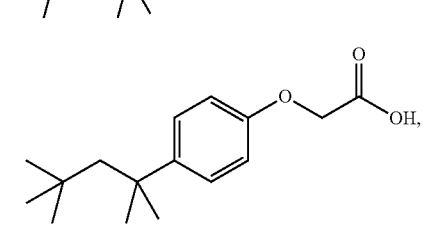

or any combination thereof. In some embodiments, for example, the herbicide may further comprise a carrier.

In accordance with certain embodiments, for instance, the root parasitic plant may comprise at least one *Orobanchaceae* species. In some embodiments, for example, the root parasitic plant may comprise at least one *Striga* species. In further embodiments, for instance, the root parasitic plant may comprise at least one of *Striga asiatica, Striga aspera, Striga forbesii, Striga hermonthica, Striga gesnerioides,* or any combination thereof.

In accordance with certain embodiments, for example, the herbicide may selectively inhibit *Striga* seed germination. In some embodiments, for instance, the herbicide may comprise a *Striga*-specific agonist. In further embodiments, for example, the at least one strigolactone receptor may comprise an ShHTL7 receptor. In such embodiments, for instance, the active compound may be selected to bind to an active site of the ShHTL7 receptor in seeds of the root parasitic plant.

In accordance with certain embodiments, for example, the host plant may comprise at least one of a monocotyledonous crop, a dicotyledonous crop, or any combination thereof. In some embodiments, for instance, the host plant may comprise at least one of sorghum, maize, millet, rice, cowpea, tomato, tobacco, carrot, clover, cucumber, sunflower, or any combination thereof.

Many modifications and other embodiments of the inventions set forth herein will come to mind to one skilled in the art to which the inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method for inhibiting germination of root parasitic plants, the method comprising applying an effective amount of a composition of to a planting area comprising a host plant before seed germination of the root parasitic plants, wherein the composition comprises an active compound represented by Formula I:

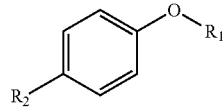

wherein $R_1$ is selected from the group consisting of:

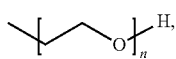

a carboxyl group, and an acyl group, wherein when $R_1$ is the carboxyl group or the acyl group, $R_1$ includes a straight chain $C_1$-$C_n$ alkyl group between O and the carboxyl group or the acyl group;

$R_2$ is a straight chain or branched $C_6$-$C_{10}$ alkyl group; and n is from 1 to 40, wherein the active compound binds to an active site of at least one strigolactone receptor in seeds of the root parasitic plant and the active compound is effective in inhibiting germination of the seeds without affecting germination of the host plant and wherein the root parasitic plants comprise at least one *Orobanchaceae* species or at least one *Striga*, species, or combinations thereof.

2. The method of claim 1, wherein applying the composition to the planting area comprising a host plant before seed germination of the root parasitic plant comprises applying the composition to the planting area during planting season.

3. The method of claim 1, wherein the active compound comprises at least one of

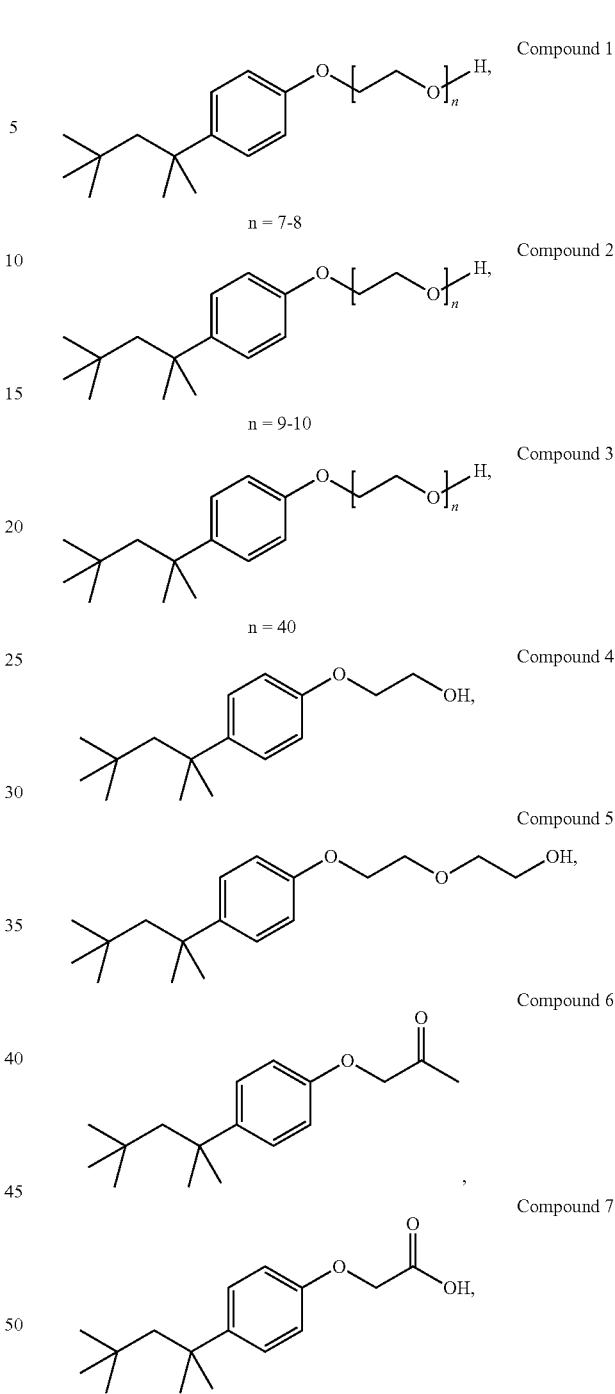

or any combination thereof.

4. The method claim 1, wherein the root parasitic plants comprise at least one *Striga*, species, selected from the group consisting of *Striga asiatica, Striga aspera, Striga forbesii, Striga hermonthica, Striga* gesnerioides, and combinations thereof.

5. The method of claim 1, wherein the host plant is a monocotyledonous crop, a dicotyledonous crop, or any combination thereof.

6. The method of claim 1, wherein the active compound is a *Striga*-specific herbicide.

7. The method of claim 1, wherein the active compound is, a *Striga*-specific agonist.

8. The method of claim 1, wherein the at least one strigolactone receptor comprises an ShHTL7 receptor, and wherein the active compound is selected to bind to an active site of the ShHTL7 receptor in seeds of the root parasitic plant.

9. The method of claim 5, wherein the host plant is selected from the group consisting of sorghum, maize, millet, rice, cowpea, tomato, tobacco, carrot, clover, cucumber, sunflower, and combinations thereof.

10. The method of claim 6, wherein the composition selectively inhibits *Striga* seed germination.

\* \* \* \* \*